US011785967B2

(12) United States Patent
Vafeiadi et al.

(10) Patent No.: US 11,785,967 B2
(45) Date of Patent: Oct. 17, 2023

(54) SUGAR REDUCTION OF FOOD PRODUCTS

(71) Applicant: SOCIÉTÉ DES PRODUITS NESTLÉ S.A., Vevey (CH)

(72) Inventors: Christina Vafeiadi, Lausanne (CH); Simon Johansson, Anderstorp (SE); Juan Sanz-Valero, Columbus, OH (US); Pu-Sheng Cheng, Dublin, OH (US); Charlotte Gancel, Lausanne (CH); Sean Christopher Austin, Mezieres (CH); Gilles Bourdin, Fribourg (CH)

(73) Assignee: Societe des Produits Nestle S.A., Vevey (CH)

( * ) Notice: Subject to any disclaimer, the term of this patent is extended or adjusted under 35 U.S.C. 154(b) by 0 days.

(21) Appl. No.: 15/569,139

(22) PCT Filed: Apr. 21, 2016

(86) PCT No.: PCT/EP2016/058948
§ 371 (c)(1),
(2) Date: Oct. 25, 2017

(87) PCT Pub. No.: WO2016/173929
PCT Pub. Date: Nov. 3, 2016

(65) Prior Publication Data
US 2018/0146699 A1    May 31, 2018

Related U.S. Application Data

(60) Provisional application No. 62/154,311, filed on Apr. 29, 2015.

(51) Int. Cl.
*A23L 2/02* (2006.01)
*C12P 19/18* (2006.01)
(Continued)

(52) U.S. Cl.
CPC ............ *A23L 2/02* (2013.01); *A23G 3/366* (2013.01); *A23L 33/175* (2016.08);
(Continued)

(58) Field of Classification Search
CPC ...... C12N 9/1051; C12N 9/1048; C12P 19/18; C12P 18/18; A23L 33/175; A23L 2/02; A23L 33/17; A23G 3/366; A23P 10/35
See application file for complete search history.

(56) References Cited

U.S. PATENT DOCUMENTS 6,042,823 A * 3/2000 Kimura ............ C12Y 204/0101
424/94.5
2008/0008791 A1 * 1/2008 Aldred ................... A23G 9/327
426/101
(Continued)

FOREIGN PATENT DOCUMENTS

EP          1987726       11/2008
KR     20110032480 A  *  3/2011
(Continued)

OTHER PUBLICATIONS

Kothari et al Immobilization of glucansucrase for the production of gluco-oligosaccharides from Leuconostoc mesenteroides, Biotechnology letter (2012) 34: 2101-2106.*
(Continued)

*Primary Examiner* — Changqing Li
(74) *Attorney, Agent, or Firm* — K&L Gates LLP

(57) ABSTRACT

A process for reducing the monosaccharide and/or disaccharide content in a food material, the process comprising contacting the food material with a glucosyltransferase that comprises an amino acid sequence having at least 95% identity to SEQ ID NO: 1.

15 Claims, 8 Drawing Sheets
Specification includes a Sequence Listing.

(51) Int. Cl.
  *C12N 9/10* (2006.01)
  *A23G 3/36* (2006.01)
  *A23L 33/175* (2016.01)

(52) U.S. Cl.
  CPC ............ *C12N 9/1051* (2013.01); *C12P 19/18* (2013.01); *C12Y 204/01005* (2013.01); *A23V 2002/00* (2013.01)

(56) References Cited

U.S. PATENT DOCUMENTS

| | | | | |
|---|---|---|---|---|
| 2013/0216652 | A1* | 8/2013 | Sans-Valero | A23L 2/385 426/51 |
| 2016/0122445 | A1* | 5/2016 | Nambiar | C08B 37/0021 514/59 |
| 2017/0006902 | A1* | 1/2017 | Garske | C12Y 204/01 |
| 2018/0049457 | A1* | 2/2018 | Cheng | A61K 31/716 |

FOREIGN PATENT DOCUMENTS

| | | | | |
|---|---|---|---|---|
| WO | 03008618 | | 1/2003 | |
| WO | WO-03008618 | A2 * | 1/2003 | ........... C12N 9/1051 |

OTHER PUBLICATIONS

Nguyen, "Production of a low calorie mandarin juice by enzymatic conversion of constituent sugars to oligosaccharides and prevention of insoluble glucan formation", Biotechnol Letter, 2015, 37, pp. 711-716 (Year: 2015).*

Pijning, "Biochemical and crystallographic characterization of a glucansucrase from Lactobacillus reuteri 180", Biocatalysis and Biotransformation, 2008, 26(1-2), pp. 12-17 (Year: 2008).*

Rabelo, "Enzyme synthesis of oligosaccharide using cashew apple juice as substrate", Bioresource Technology, 2009, 100, pp. 5574-5580 (Year: 2009).*

Braverman, The pH Levels of Apple, Orange, Grape & Cranberry Fruit Juices, [Online], published Nov. 27, 2018, [retrieved on May 22, 2023]. Retrieved from the Internet: <URL: https://www.weekand.com/healthy-living/article/ph-levels-apple-orange-grape-cranberry-fruit-juices-18020029.php> (Year: 2018).*

Kralj et al. "Glucan synthesis in the genus *Lactobacillus*: isolation and characterization of glucansucrase genes, enzymes and glucan products from six different strains" Microbiology, 2004, vol. 150, pp. 3681-3690, XP002354989.

Johansson et al. "Oligosaccharide Synthesis in Fruit Juice Concentrates Using a Glucansucrase From Lactobacillus reuteri 180" Food and Bioproducts Processing, 2016, vol. 98, pp. 201-209.

* cited by examiner

A

B

C

D

A

B

C

A

B

C

A

C

B

SEQUENCE LISTING

```
<160> NUMBER OF SEQ ID NOS: 1

<210> SEQ ID NO 1
<211> LENGTH: 1772
<212> TYPE: PRT
<213> ORGANISM: Lactobacillus reuteri

<400> SEQUENCE: 1

Met Glu Ile Lys Lys His Phe Lys Leu Tyr Lys Ser Gly Lys Gln Trp
1               5                   10                  15

Val Thr Ala Ala Val Ala Thr Val Ala Val Ser Thr Ala Leu Leu Tyr
            20                  25                  30

Gly Gly Val Ala His Ala Asp Gln Gln Val Gln Ser Ser Thr Thr Gln
        35                  40                  45

Glu Gln Thr Ser Thr Val Asn Ala Asp Thr Thr Lys Thr Val Asn Leu
    50                  55                  60

Asp Thr Asn Thr Asp Gln Pro Ala Gln Thr Thr Asp Lys Asn Gln Val
65                  70                  75                  80

Ala Asn Asp Thr Thr Thr Asn Gln Ser Lys Thr Asp Ser Thr Ser Thr
                85                  90                  95

Thr Val Lys Asn Pro Thr Phe Ile Pro Val Ser Thr Leu Ser Ser Ser
```

```
            100                 105                 110
Asp Asn Glu Lys Gln Ser Gln Asn Tyr Asn Lys Pro Asp Asn Gly Asn
            115                 120                 125

Tyr Gly Asn Val Asp Ala Ala Tyr Phe Asn Asn Gln Leu His Ile
130                 135                 140

Ser Gly Trp His Ala Thr Asn Ala Ser Gln Gly Thr Asp Ser Arg Gln
145                 150                 155                 160

Val Ile Val Arg Asp Ile Thr Thr Lys Thr Glu Leu Gly Arg Thr Asn
                165                 170                 175

Val Thr Asn Asn Val Leu Arg Pro Asp Val Lys Asn Val His Asn Val
            180                 185                 190

Tyr Asn Ala Asp Asn Ser Gly Phe Asp Val Asn Ile Asn Ile Asp Phe
            195                 200                 205

Ser Lys Met Lys Asp Tyr Arg Asp Ser Ile Glu Ile Val Ser Arg Tyr
            210                 215                 220

Ser Gly Asn Gly Lys Ser Val Asp Trp Trp Ser Gln Pro Ile Thr Phe
225                 230                 235                 240

Asp Lys Asn Asn Tyr Ala Tyr Leu Asp Thr Phe Glu Val Lys Asn Gly
                245                 250                 255

Glu Leu His Ala Thr Gly Trp Asn Ala Thr Asn Lys Ala Ile Asn Tyr
            260                 265                 270

Asn His His Phe Val Ile Leu Phe Asp Arg Thr Asn Gly Lys Glu Val
            275                 280                 285

Thr Arg Gln Glu Val Arg Asp Gly Gln Ser Arg Pro Asp Val Ala Lys
290                 295                 300

Val Tyr Pro Gln Val Val Gly Ala Asn Asn Ser Gly Phe Asp Val Thr
305                 310                 315                 320

Phe Asn Ile Gly Asp Leu Asp Tyr Thr His Gln Tyr Gln Ile Leu Ser
                325                 330                 335

Arg Tyr Ser Asn Ala Asp Asn Gly Glu Gly Asp Tyr Val Thr Tyr Trp
            340                 345                 350

Phe Ala Pro Gln Ser Ile Ala Pro Ala Asn Gln Ser Asn Gln Gly Tyr
            355                 360                 365

Leu Asp Ser Phe Asp Ile Ser Lys Asn Gly Glu Val Thr Val Thr Gly
            370                 375                 380

Trp Asn Ala Thr Asp Leu Ser Glu Leu Gln Thr Asn His Tyr Val Ile
385                 390                 395                 400

Leu Phe Asp Gln Thr Ala Gly Gln Gln Val Ala Ser Ala Lys Val Asp
                405                 410                 415

Leu Ile Ser Arg Pro Asp Val Ala Lys Ala Tyr Pro Thr Val Lys Thr
            420                 425                 430

Ala Glu Thr Ser Gly Phe Lys Val Thr Phe Lys Val Ser Asn Leu Gln
            435                 440                 445

Pro Gly His Gln Tyr Ser Val Val Ser Arg Phe Ser Ala Asp Glu Asn
            450                 455                 460

Gly Asn Gly Asn Asp Lys Arg His Thr Asp Tyr Trp Tyr Ser Pro Val
465                 470                 475                 480

Thr Leu Asn Gln Thr Ala Ser Asn Ile Asp Thr Ile Thr Met Thr Ser
                485                 490                 495

Asn Gly Leu His Ile Thr Gly Trp Met Ala Ser Asp Asn Ser Ile Asn
            500                 505                 510

Glu Ala Thr Pro Tyr Ala Ile Ile Leu Asn Asn Gly Arg Glu Val Thr
            515                 520                 525
```

```
Arg Gln Lys Leu Thr Leu Ile Ala Arg Pro Asp Val Ala Val Tyr
            530                 535                 540

Pro Ser Leu Tyr Asn Ser Ala Val Ser Gly Phe Asp Thr Ile Lys
545                 550                 555                 560

Leu Thr Asn Ala Gln Tyr Gln Ala Leu Asn Gly Gln Leu Gln Val Leu
                565                 570                 575

Leu Arg Phe Ser Lys Ala Val Asp Gly Asn Pro Asn Gly Thr Asn Thr
                580                 585                 590

Val Thr Asp Gln Phe Ser Lys Asn Tyr Ala Thr Thr Gly Gly Asn Phe
                595                 600                 605

Asp Tyr Val Lys Val Asn Gly Asn Gln Ile Glu Phe Ser Gly Trp His
                610                 615                 620

Ala Thr Asn Gln Ser Asn Asp Lys Asn Ser Gln Trp Ile Ile Val Leu
625                 630                 635                 640

Val Asn Gly Lys Glu Val Lys Arg Gln Leu Val Asn Asp Thr Lys Asp
                645                 650                 655

Gly Ala Ala Gly Phe Asn Arg Asn Asp Val Tyr Lys Val Asn Pro Ala
                660                 665                 670

Ile Glu Asn Ser Ile Met Ser Gly Phe Gln Gly Ile Ile Thr Leu Pro
                675                 680                 685

Val Thr Val Lys Asp Glu Asn Val Gln Leu Val His Arg Phe Ser Asn
                690                 695                 700

Asp Ala Lys Thr Gly Glu Gly Asn Tyr Val Asp Phe Trp Ser Glu Val
705                 710                 715                 720

Met Ser Val Lys Asp Ser Phe Gln Lys Gly Asn Gly Pro Leu Asn Gln
                725                 730                 735

Phe Gly Leu Gln Thr Ile Asn Gly Gln Gln Tyr Tyr Ile Asp Pro Thr
                740                 745                 750

Thr Gly Gln Pro Arg Lys Asn Phe Leu Leu Gln Asn Gly Asn Asp Trp
                755                 760                 765

Ile Tyr Phe Asp Lys Asp Thr Gly Ala Gly Thr Asn Ala Leu Lys Leu
                770                 775                 780

Gln Phe Asp Lys Gly Thr Ile Ser Ala Asp Glu Gln Tyr Arg Arg Gly
785                 790                 795                 800

Asn Glu Ala Tyr Ser Tyr Asp Asp Lys Ser Ile Glu Asn Val Asn Gly
                805                 810                 815

Tyr Leu Thr Ala Asp Thr Trp Tyr Arg Pro Lys Gln Ile Leu Lys Asp
                820                 825                 830

Gly Thr Thr Trp Thr Asp Ser Lys Glu Thr Asp Met Arg Pro Ile Leu
                835                 840                 845

Met Val Trp Trp Pro Asn Thr Val Thr Gln Ala Tyr Tyr Leu Asn Tyr
850                 855                 860

Met Lys Gln Tyr Gly Asn Leu Leu Pro Ala Ser Leu Pro Ser Phe Ser
865                 870                 875                 880

Thr Asp Ala Asp Ser Ala Glu Leu Asn His Tyr Ser Glu Leu Val Gln
                885                 890                 895

Gln Asn Ile Glu Lys Arg Ile Ser Glu Thr Gly Ser Thr Asp Trp Leu
                900                 905                 910

Arg Thr Leu Met His Glu Phe Val Thr Lys Asn Ser Met Trp Asn Lys
                915                 920                 925

Asp Ser Glu Asn Val Asp Tyr Gly Gly Leu Gln Leu Gln Gly Gly Phe
                930                 935                 940
```

```
Leu Lys Tyr Val Asn Ser Asp Leu Thr Lys Tyr Ala Asn Ser Asp Trp
945                 950                 955                 960

Arg Leu Met Asn Arg Thr Ala Thr Asn Ile Asp Gly Lys Asn Tyr Gly
            965                 970                 975

Gly Ala Glu Phe Leu Leu Ala Asn Asp Ile Asp Asn Ser Asn Pro Val
            980                 985                 990

Val Gln Ala Glu Glu Leu Asn Trp Leu Tyr Tyr Leu Met Asn Phe Gly
            995                 1000                1005

Thr Ile Thr Gly Asn Asn Pro Glu Ala Asn Phe Asp Gly Ile Arg Val
1010                1015                1020

Asp Ala Val Asp Asn Val Asp Val Asp Leu Leu Ser Ile Ala Arg Asp
1025                1030                1035                1040

Tyr Phe Asn Ala Ala Tyr Asn Met Glu Gln Ser Asp Ala Ser Ala Asn
                1045                1050                1055

Lys His Ile Asn Ile Leu Glu Asp Trp Gly Trp Asp Pro Ala Tyr
                1060                1065                1070

Val Asn Lys Ile Gly Asn Pro Gln Leu Thr Met Asp Asp Arg Leu Arg
                1075                1080                1085

Asn Ala Ile Met Asp Thr Leu Ser Gly Ala Pro Asp Lys Asn Gln Ala
                1090                1095                1100

Leu Asn Lys Leu Ile Thr Gln Ser Leu Val Asn Arg Ala Asn Asp Asn
1105                1110                1115                1120

Thr Glu Asn Ala Val Ile Pro Ser Tyr Asn Phe Val Arg Ala His Asp
                1125                1130                1135

Ser Asn Ala Gln Asp Gln Ile Arg Gln Ala Ile Gln Ala Ala Thr Gly
                1140                1145                1150

Lys Pro Tyr Gly Glu Phe Asn Leu Asp Asp Glu Lys Lys Gly Met Glu
                1155                1160                1165

Ala Tyr Ile Asn Asp Gln Asn Ser Thr Asn Lys Lys Trp Asn Leu Tyr
                1170                1175                1180

Asn Met Pro Ser Ala Tyr Thr Ile Leu Leu Thr Asn Lys Asp Ser Val
1185                1190                1195                1200

Pro Arg Val Tyr Tyr Gly Asp Leu Tyr Gln Asp Gly Gly Gln Tyr Met
                1205                1210                1215

Glu His Lys Thr Arg Tyr Phe Asp Thr Ile Thr Asn Leu Leu Lys Thr
                1220                1225                1230

Arg Val Lys Tyr Val Ala Gly Gly Gln Thr Met Ser Val Asp Lys Asn
                1235                1240                1245

Gly Ile Leu Thr Asn Val Arg Phe Gly Lys Gly Ala Met Asn Ala Thr
    1250                1255                1260

Asp Thr Gly Thr Asp Glu Thr Arg Thr Glu Gly Ile Gly Val Val Ile
1265                1270                1275                1280

Ser Asn Asn Thr Asn Leu Lys Leu Asn Asp Gly Glu Ser Val Val Leu
                1285                1290                1295

His Met Gly Ala Ala His Lys Asn Gln Lys Tyr Arg Ala Val Ile Leu
                1300                1305                1310

Thr Thr Glu Asp Gly Val Lys Asn Tyr Thr Asn Asp Thr Asp Ala Pro
                1315                1320                1325

Val Ala Tyr Thr Asp Ala Asn Gly Asp Leu His Phe Thr Asn Thr Asn
                1330                1335                1340

Leu Asp Gly Gln Gln Tyr Thr Ala Val Arg Gly Tyr Ala Asn Pro Asp
1345                1350                1355                1360

Val Thr Gly Tyr Leu Ala Val Trp Val Pro Ala Gly Ala Ala Asp Asp
```

```
                    1365              1370              1375
Gln Asp Ala Arg Thr Ala Pro Ser Asp Glu Ala His Thr Thr Lys Thr
            1380              1385              1390
Ala Tyr Arg Ser Asn Ala Ala Leu Asp Ser Asn Val Ile Tyr Glu Gly
        1395              1400              1405
Phe Ser Asn Phe Ile Tyr Trp Pro Thr Thr Glu Ser Glu Arg Thr Asn
    1410              1415              1420
Val Arg Ile Ala Gln Asn Ala Asp Leu Phe Lys Ser Trp Gly Ile Thr
1425              1430              1435              1440
Thr Phe Glu Leu Ala Pro Gln Tyr Asn Ser Ser Lys Asp Gly Thr Phe
                1445              1450              1455
Leu Asp Ser Ile Ile Asp Asn Gly Tyr Ala Phe Thr Asp Arg Tyr Asp
            1460              1465              1470
Leu Gly Met Ser Thr Pro Asn Lys Tyr Gly Ser Asp Glu Asp Leu Arg
        1475              1480              1485
Asn Ala Leu Gln Ala Leu His Lys Ala Gly Leu Gln Ala Ile Ala Asp
    1490              1495              1500
Trp Val Pro Asp Gln Ile Tyr Asn Leu Pro Gly Lys Glu Ala Val Thr
1505              1510              1515              1520
Val Thr Arg Ser Asp Asp His Gly Thr Thr Trp Glu Val Ser Pro Ile
                1525              1530              1535
Lys Asn Val Val Tyr Ile Thr Asn Thr Ile Gly Gly Gly Glu Tyr Gln
            1540              1545              1550
Lys Lys Tyr Gly Gly Glu Phe Leu Asp Thr Leu Gln Lys Glu Tyr Pro
        1555              1560              1565
Gln Leu Phe Ser Gln Val Tyr Pro Val Thr Gln Thr Thr Ile Asp Pro
    1570              1575              1580
Ser Val Lys Ile Lys Glu Trp Ser Ala Lys Tyr Phe Asn Gly Thr Asn
1585              1590              1595              1600
Ile Leu His Arg Gly Ala Gly Tyr Val Leu Arg Ser Asn Asp Gly Lys
                1605              1610              1615
Tyr Tyr Asn Leu Gly Thr Ser Thr Gln Gln Phe Leu Pro Ser Gln Leu
            1620              1625              1630
Ser Val Gln Asp Asn Glu Gly Tyr Gly Phe Val Lys Glu Gly Asn Asn
        1635              1640              1645
Tyr His Tyr Tyr Asp Glu Asn Lys Gln Met Val Lys Asp Ala Phe Ile
    1650              1655              1660
Gln Asp Ser Val Gly Asn Trp Tyr Tyr Phe Asp Lys Asn Gly Asn Met
1665              1670              1675              1680
Val Ala Asn Gln Ser Pro Val Glu Ile Ser Asn Gly Ala Ser Gly
                1685              1690              1695
Thr Tyr Leu Phe Leu Asn Asn Gly Thr Ser Phe Arg Ser Gly Leu Val
            1700              1705              1710
Lys Thr Asp Ala Gly Thr Tyr Tyr Tyr Asp Gly Asp Gly Arg Met Val
        1715              1720              1725
Arg Asn Gln Thr Val Ser Asp Gly Ala Met Thr Tyr Val Leu Asp Glu
    1730              1735              1740
Asn Gly Lys Leu Val Ser Glu Ser Phe Asp Ser Ser Ala Thr Glu Ala
1745              1750              1755              1760
His Pro Leu Lys Pro Gly Asp Leu Asn Gly Gln Lys
                1765              1770
```

SUGAR REDUCTION OF FOOD PRODUCTS

CROSS REFERENCE TO RELATED APPLICATIONS

The present application is a National Stage of International Application No. PCT/EP2016/058948, filed on Apr. 21, 2016, which claims priority to U.S. Provisional Patent Application No. 62/154,311, filed on Apr. 29, 2015, the entire contents of which are being incorporated herein by reference.

FIELD OF INVENTION

The invention relates to a process for reducing the intrinsic sugar content of food materials using in situ enzymatic reactions, and to food materials produced by the process.

BACKGROUND

Fruit based products like juices are a valuable source of vitamins but are high in calories since they contain high levels of intrinsic sugars (mono and disaccharides). Recent studies have shown that high consumption of simple sugars have negative health effects. For example, high sugar intake is associated with diseases such as obesity, type II diabetes and cardiovascular disease. According to recent recommendations by the World Health Organisation, only 10% of the total daily calorie intake should come from free sugars (World health organisation (2014), *WHO open public consultation on draft sugar guideline*).

There is therefore a need to reduce intrinsic sugar content in food products. One such approach is selective fermentation using immobilized cells to eliminate sugars. *Zmomonas mobiliz* may be used to eliminate glucose, fructose and sucrose while yeast *Saccharomyces cerevisiae* may be used to remove glucose, fructose, maltose and sucrose completely, and isomaltose and maltotriose partially (Goffin et al., 2011, Critical reviews in Food Science and Nutrition, 51, 394-409). However, this approach is time consuming, expensive, requires highly controlled conditions and results in the formation of by-products (e.g. acids and ethanol) which have a major impact on taste and flavour.

Another approach is membrane separation wherein mono- and disaccharides are separated from the remaining food product (Goffin et al., 2011, Critical reviews in Food Science and Nutrition.51, 394-409). However, this process is associated with low efficiency, requires expensive equipment and leads to loss of micronutrients and mass in the food product.

Oligosaccharides such as isomalto-oligosaccharides, galacto-oligosaccharides and gluco-oligosaccharides are found naturally in foods and many of them cannot be digested by humans. Certain oligosaccharides are known to have a prebiotic effect and have been added to beverages, infant milk powders, confectionery product, bakery products, yogurts and dairy desserts.

Although oligosaccharides are usually added as functional food additives to different products after being enzymatically produced from pure sugars, some recent reports propose to enzymatically produce oligosaccharides using sugars already present in the food products. For example, US 2009/0297660 discloses producing galacto-oligosaccharides in cream cheese products by using the lactose contained in the dairy substrate. US 2010/0040728 relates to in situ reduction of sucrose in beverages by converting sucrose to fructo-oligosaccharides. Furthermore, EP 0458358 B1 discloses a process for producing skim milk powder containing galacto-oligosaccharides using the lactose present in milk as substrate by contacting concentrated milk with beta-galactosidase.

There is still a need in the industry to efficiently reduce intrinsic sugars in food materials such as fruit juices in order to provide nutritional and health benefits in the resulting products. The present invention addresses this need.

SUMMARY OF THE INVENTION

The present invention provides a process of reducing intrinsic sugar content of a food material by contacting the food with a glucosyltransferase.

According to a first aspect of the present invention there is provided a process for reducing the monosaccharide and/or disaccharide content in a food material, the process comprising contacting the food material with a glucosyltransferase that comprises an amino acid sequence having at least 95% identity to SEQ ID NO:1.

Preferably the glucosyltransferase converts monosaccharides and/or disaccharides in the food material to oligosaccharides and/or polysaccharides. More preferably, the glucosyltransferase converts monosaccharides and/or disaccharides in the food material to oligosaccharides. In one embodiment the oligosaccharides comprise $\alpha$-1,3 glycosidic bonds and/or $\alpha$-1,6 glycosidic bonds.

The oligosaccharides may comprise $\alpha$-1,2 glycosidic bonds.

The glucosyltransferase may comprise an amino acid sequence having at least 97%, 98% or 99% identity to SEQ ID NO:1.

Preferably the glucosyltransferase has the amino acid sequence shown in SEQ ID NO:1.

The food material preferably comprises fruit or a component thereof. A typical food material is material that comprises fruit juice which contains sucrose.

Examples of fruit juices include orange juice, apple juice, mango juice, peach juice, banana juice, date juice, apricot juice, grapefruit juice, orange juice, papaya juice, pineapple juice, raspberry juice, strawberry juice, pear juice, tangerine juice and cherry juice.

In a preferred embodiment, the fruit juice is a sucrose containing fruit juice. The fruit juice may also comprise glucose and/or fructose.

In one embodiment the process comprises contacting the food material with the glucosyltransferase wherein the process takes place at a pH of between about 3 to 7, preferably at a pH between about 3 to 5. For example, the pH may be about 3, 3.5, 4, 4.5 or 5.

In one embodiment, the pH is about 4.5.

The process may be carried out at a temperature of, for example, about 40 to 60° C., preferably 45 to 55° C., more preferably about 50° C.

The process may involve the presence of $Ca^{++}$. The $Ca^{++}$ may be present at a concentration of, for example, 0.8-1.2 mM, preferably about 1 mM $Ca^{++}$. In one embodiment, $CaCl_2$ is added, for example at about 1 mM.

In one embodiment the process is carried out using a glucosyltransferase concentration of about 2 to 10 mg glucosyltransferase/g sucrose, about 3 to 8 mg glucosyltransferase/g sucrose, about 5 to 6 mg glucosyltransferase/g sucrose or about 5.8 mg glucosyltransferase/g sucrose.

In another embodiment the process is carried out using a glucosyltransferase concentration of about 5 to 50 U/g sucrose, about 5 to 30 U/g sucrose, about 10 to 20 U/g sucrose, about 12 to 18 U/g sucrose or about 14.5 U/g sucrose.

The activity (U) of the enzyme is preferably measured using the dextran sucrose activity assay exemplified in the Examples section.

The process may also comprise immobilising the glucosyltransferase on a support. In one embodiment, the enzymatic reaction can be terminated by removing the immobilised enzyme from contact with the food material.

In one embodiment, the total combined monosaccharide and disaccharide content in the food material may be reduced by, for example, at least 5%, 10%, 20%, 25%, 30%, 35% or 40%.

In one embodiment, the sucrose level in the food material may reduced by at least 10%, 20%, 40%, 60%, 80%, 90%, 95%, 97% or 99%.

In one embodiment the food material contains at least 5%, 7% or 10% oligosaccharides based on the dry weight of the food material, after exposure to the glucosyltransferase.

The glucosyltransferase enzymatic reaction may be terminated by, for example applying heat or conducting pasteurisation.

The process of the invention may further comprise contacting the food material with a fructosyltransferase, either simultaneously or sequentially with the glucosyltransferase.

According to another aspect of the present invention there is provided a food material produced by the process of the invention. The food material may be obtainable, for example obtained, by the process of the invention. The food material may comprise oligosaccharides which comprise α-1,2 glycosidic bonds.

Preferably the food material has reduced intrinsic sugar levels and increased oligosaccharides levels compared to a food material that is not subjected to the process of the invention.

The food material may be further processed into a confectionery product.

According to another aspect of the present invention there is provided use of a glucosyltransferase that comprises an amino acid sequence having at least 95%, 96%, 97%, 98% or 99% identity to SEQ ID NO:1, or has an amino acid sequence of SEQ ID NO:1, for reducing the monosaccharide and/or disaccharide content of a food material.

According to another aspect of the present invention there is provided use of a glucosyltransferase that comprises an amino acid sequence having at least 95%, 96%, 97%, 98% or 99% identity to SEQ ID NO:1, or has an amino acid sequence of SEQ ID NO:1 for increasing the oligosaccharide and/or polysaccharide content of a food material.

According to another aspect of the present invention there is provided use of a glucosyltransferase that comprises an amino acid sequence having at least 95%, 96%, 97%, 98% or 99% identity to SEQ ID NO:1, or has an amino acid sequence of SEQ ID NO:1 for reducing the monosaccharide and/or disaccharide content and increasing the oligosaccharide or polysaccharide content of a food material.

DETAILED DESCRIPTION OF THE INVENTION

The present invention provides a process for reducing the monosaccharide and/or disaccharide content in a food material, the process comprising contacting the food material with a glucosyltransferase that comprises an amino acid sequence having at least 95% identity to SEQ ID NO:1.

Glucosyltransferase

Glucosyltransferases (GTF) are transglucosidase enzymes (EC 2.4.1.-) that may use sucrose as substrate to synthesize glucoconjugates, oligosaccharides and polysaccharides using the energy of the glycosidic bond of sucrose to transfer a corresponding glycosyl moiety (Monsan et al., 2000, Food Biotechnology. Amsterdam, Elsevier Science, pp 115-122; Monsan, 2001, International Dairy Journal 11,675-685). Glucosyltransferases may catalyse three types of reactions; polymerization, hydrolysis and an acceptor reaction.

Catalysis by glucosyltransferases using sucrose as a substrate starts with sucrose binding to the active site of the enzyme and the cleavage of the α-1,2 glycosidic linkage between glucose and fructose yielding a covalent glycosyl-enzyme intermediate and a liberated fructose molecule. It is the nature of the acceptor substrate which determines which reaction will occur. The simplest reaction is hydrolysis of sucrose into glucose and fructose using water as acceptor. The glycosyl intermediate can be transferred to a growing α-glucan chain in the polymerization reaction (Leemhuis et al., 2012, Biocatalysis and Biotransformation 30,366-376). The glycosyl moiety from sucrose can also be transferred to an acceptor molecule (e.g. glucose, fructose, maltose or a non-carbohydrate acceptor) instead of the growing polymer chain in a so called acceptor reaction yielding either an sucrose isomer, an oligosaccharide or a glucoconjugate (Demuth et al., 2000, *Food Biotechnology*. Amsterdam, Elsevier Science, 2000, pp 123-135; Monsan, 2001, International Dairy Journal 11,675-685). A well-known product from the acceptor reaction is leucrose, a sucrose isomer which is formed when fructose acts as acceptor forming an α-1,5 glycosidic linkage (Leemhuis et al., 2012, Biocatalysis and Biotransformation 30,366-376).

In the absence of residual sucrose in the reaction medium, glucosyltransferases may catalyse disproportionation reactions of oligosaccharides as substrates (Monsan, 2001, International Dairy Journal 11,675-685).

The types of α-glycosidic linkages that may be formed between two glucose moieties are α-1,2; α-1,3; α-1,4 and α-1,6. Examples of α-glucans produced are:
  dextran with a backbone of α-1,6 glycosidic linkages
  mutan containing mainly α-1,3 glycosidic linkages
  alternan containing alternating α-1,6 /α-1,3 glycosidic linkages
  reuteran with randomly distributed α-1,4 or α-1,6 glycosidic linkages
  amylose containing α-1,4 glycosidic linkages
  NMR spectroscopy can be used to determine the types and ratio of linkages in α-glucans.

The glucosyltransferase used in the process of the present invention preferably has least 95, 96, 97, 98, or 99% identity to SEQ ID NO:1.

(SEQ ID NO: 1)
MEIKKHFKLYKSGKQWVTAAVATVAVSTALLYGGVAHADQQVQSSTTQEQ

TSTVNADTTKTVNLDTNTDQPAQTTDKNQVANDTTTNQSKTDSTSTTVKN

PTFIPVSTLSSSDNEKQSQNYNKPDNGNYGNVDAAYFNNNQLHISGWHAT

NASQGTDSRQVIVRDITTKTELGRTNVTNNVLRPDVKNVHNVYNADNSGF

DVNINIDFSKMKDYRDSIEIVSRYSGNGKSVDWWSQPITFDKNNYAYLDT

FEVKNGELHATGWNATNKAINYNHHFVILFDRTNGKEVTRQEVRDGQSRP

-continued

DVAKVYPQVVGANNSGFDVTFNIGDLDYTHQYQILSRYSNADNGEGDYVT

YWFAPQSIAPANQSNQGYLDSFDISKNGEVTVTGWNATDLSELQTNHYVI

LFDQTAGQQVASAKVDLISRPDVAKAYPTVKTAETSGFKVTFKVSNLQPG

HQYSVVSRFSADENGNGNDKRHTDYWYSPVTLNQTASNIDTITMTSNGLH

ITGWMASDNSINEATPYAIILNNGREVTRQKLTLIARPDVAAVYPSLYNS

AVSGFDTTIKLTNAQYQALNGQLQVLLRFSKAVDGNPNGTNTVTDQFSKN

YATTGGNFDYVKVNGNQIEFSGWHATNQSNDKNSQWIIVLVNGKEVKRQL

VNDTKDGAAGFNRNDVYKVNPAIENSIMSGFQGIITLPVTVKDENVQLVH

RFSNDAKTGEGNYVDFWSEVMSVKDSFQKGNGPLNQFGLQTINGQQYYID

PTTGQPRKNFLLQNGNDWIYFDKDTGAGTNALKLQFDKGTISADEQYRRG

NEAYSYDDKSIENVNGYLTADTWYRPKQILKDGTTWTDSKETDMRPILMV

WWPNTVTQAYYLNYMKQYGNLLPASLPSFSTDADSAELNHYSELVQQNIE

KRISETGSTDWLRTLMHEFVTKNSMWNKDSENVDYGGLQLQGGFLKYVNS

DLTKYANSDWRLMNRTATNIDGKNYGGAEFLLANDIDNSNPVVQAEELNW

LYYLMNFGTITGNNPEANFDGIRVDAVDNVDVDLLSIARDYFNAAYNMEQ

SDASANKHINILEDWGWDDPAYVNKIGNPQLTMDDRLRNAIMDTLSGAPD

KNQALNKLITQSLVNRANDNTENAVIPSYNFVRAHDSNAQDQIRQAIQAA

TGKPYGEFNLDDEKKGMEAYINDQNSTNKKWNLYNMPSAYTILLTNKDSV

PRVYYGDLYQDGGQYMEHKTRYFDTITNLLKTRVKYVAGGQTMSVDKNGI

LTNVRFGKGAMNATDTGTDETRTEGIGVVISNNTNLKLNDGESVVLHMGA

AHKNQKYRAVILTTEDGVKNYTNDTDAPVAYTDANGDLHFTNTNLDGQQY

TAVRGYANPDVTGYLAVWVPAGAADDQDARTAPSDEAHTTKTAYRSNAAL

DSNVIYEGFSNFIYWPTTESERTNVRIAQNADLFKSWGITTFELAPQYNS

SKDGTFLDSIIDNGYAFTDRYDLGMSTPNKYGSDEDLRNALQALHKAGLQ

AIADWVPDQIYNLPGKEAVTVTRSDDHGTTWEVSPIKNVVYITNTIGGGE

YQKKYGGEFLDTLQKEYPQLFSQVYPVTQTTIDPSVKIKEWSAKYFNGTN

ILHRGAGYVLRSNDGKYYNLGTSTQQFLPSQLSVQDNEGYGFVKEGNNYH

YYDENKQMVKDAFIQDSVGNWYYFDKNGNMVANQSPVEISSNGASGTYLF

LNNGTSFRSGLVKTDAGTYYYDGDGRMVRNQTVSDGAMTYVLDENGKLVS

ESFDSSATEAHPLKPGDLNGQK

In a preferred embodiment, the glucosyltransferase is the glucosyltransferase from *Lactobacillus reuteri* having the UniProtKB accession number q5SBN3. This enzyme is referred to herein as C39/3 and has the amino acid sequence shown in SEQ ID NO:1.

The enzyme C39/3 produces glucans with α-1,6 and α-1,3 glycosidic linkages (Kralj et al., 2004, *Microbiology* 150 (Pt11):3681-3690).

In a particularly preferred embodiment, the glucosyltransferase has an amino sequence comprising or consisting of the sequence of SEQ ID NO:1, Preferably the glucosyltransferase used in the process of the present invention has substantially the same activity as the glucosyltransferase having an amino sequence of SEQ ID NO:1. The activity may be measured, for example, using the dextran sucrose activity assay, a colorimetric assay that involves the following reaction:

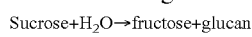
Sucrose+$H_2O$→fructose+glucan

Example Assay Conditions and Disclosed in Example 1
Fructosyltransferase

Fructosyltransferases (FTFS) catalyze three types of reactions with sucrose: polymerization of fructose into fructan polymers, hydrolysis of sucrose into fructose and glucose and oligosaccharide synthesis by transferase of fructose to an acceptor molecule (van Hijum et al., 2003 *FEBS Letters* 534, 207-210).

Fructosyltransferases may be derived from plant sources such as asparagus, sugar beet, onions, Jerusalem artichokes and others (See, Henry, R. J. et al., (1980) Phytochem. 19: 1017-1020; Unger, C. (1994) Plant Physiol. 104: 1351-1357; and Luscher, M. et al., (2000) Plant Physiol. 124:1217-122).

Fructosyltransferase may also be derived from fungal sources, such as *Aspergillus, Aureobasidium* and *Fusarium*. More specific examples include *Aspergillus japonicus,* such as CCRC 3801 1; *Aspergillus niger,* such as ATCC 20611; *Aspergillus foetidus* (such as NRRL 337); *Aspergillus aculeatus; Aureobasidium pullulans,* such as ATCC 9348, ATCC 12535; and ATCC 15223 (See, Yuan-Chi Su et al., (1993) Proceedings National Science Council, ROC 17:62-69; Hirayama, M. et al., (1989) Agric. Bioi. Chem. 53: 667-673; Hidaka, H., et al., (1988) Agric. Bioi. Chem. 52: 1181-1187; Boddy, L. M. et al., (1993) Curro Genet. 24:60-66; and U.S. Pat. No. 4,276,379).

Fructosyltransferases additionally may be derived from bacterial sources, such as *Arthrobacter* (Fouet, A. (1986) Gene 45:221-225; Sato, Y. et al. (1989) Infect. Immun. 56: 1956-1960; and Aslanidis, C. et al., (1989) J. Bacteriol, 111: 6753-6763).

In some instances, the fructosyltransferase may be a variant of a naturally occurring fructosyltransferase. Reference is made to U.S. Pat. No. 6,566,111, wherein a β-fructofuranosidase was genetically engineered to improve the productivity of the enzyme (see also US Patent Application Publication No. 20020192771 to Koji Y., et al.).

Enzyme Immobilization

As mentioned above, in embodiments of the process of the invention, the enzyme(s) used may be immobilized before contacting the food product. Such immobilization techniques are well known in the art. Examples of immobilization techniques include:

Covalent binding: In this method, enzymes are covalently linked to a support through the functional groups in the enzymes that are not essential for the catalytic activity. Oxides materials such as alumina, silica, and silicated alumina can be used for covalent binding of the enzyme.

Entrapment: The entrapment method is based on the localization of an enzyme within the lattice of a polymer matrix or membrane. Entrapment methods are classified into five major types: lattice, microcapsule, liposome, membrane, and reverse micelle. The enzyme is entrapped in the matrix of various synthetic or natural polymers. Alginate, a naturally occurring polysaccharide that forms gels by ionotropic gelation is one such immobilzation matrix.

Physical adsorption: Physical adsorption is the simplest and the oldest method of immobilizing enzymes onto carriers. Immobilization by adsorption is based on the physical interactions between the enzymes and the carrier, such as hydrogen bonding, hydrophobic interactions, van der Waals force, and their combinations. Adsorption is generally less disruptive to the enzymes than chemical means of attachment.

Cross-linking: The cross-linking method utilizes bi- or multifunctional compounds, which serve as the reagent for intermolecular cross-linking of the enzymes. Cross-linking may be used in combination with other immobilization methods such as adsorption or entrapment.

Sugars, oligosaccharides and polysaccharides

Sugars include, inter alia, monosaccharides and disaccharides such as glucose, fructose, galactose, sucrose, lactose, maltose, and trehalose. By way of example, sucrose is a disaccharide comprised of D-glucose and D-fructose wherein the C-1 carbon atom of the glucose and the C-2 carbon atom of the fructose participate in the glycoside linkage.

The term "disaccharide" as used herein refers to any compound that comprises two covalently linked monosaccharide units.

The term "oligosaccharide" as used herein refers to a compound having two to about ten monosaccharide units joined by glycosidic linkages. Preferably the oligosaccharide referred to herein has at least three monosaccharide units. In a preferred embodiment, the oligosaccharides include slowly digestible and/or non-digestible oligosaccharides (NDOs). Such oligosaccharides resist hydrolysis by digestive enzymes.

The "polysaccharide" referred to herein preferably has more than ten monosaccharide units joined by glycosidic linkages.

Different linkages present within the oligosaccharides and/or polysaccharides produced are digestible to different extents. For example, α-1,6 linkages may be considered fully, but slowly, digestible; α-1,4 linkages may be considered fully digestible; α-1,3 linkages may be considered non-digestible and α-1,2 linkages may be considered non-digestible, depending on the size and the branching pattern of the oligosaccharides.

Food Material

The food material referred to herein preferably comprises intrinsic sugars such as sucrose and/or glucose among possible sugars.

The food material may comprise fruit or a component thereof. Preferably the food product comprises fruit juice such as, but not limited to juice derived from an orange, apple, mango, peach, banana, date, apricot, grape fruit, papaya, pineapple, raspberry, strawberry, pear, tangerine and/or cherry.

The food material may, for example be fruit juice or may be in the form of a fruit puree which comprises fruit juice among other fruit components.

The food material may be further processed. For example, the food material may be further processed into a food product. The food material may comprise fruit or a component thereof and be further processed into a food product. The food product may be a dairy product, for example a fruit yoghurt; a beverage, for example a powdered fruit beverage mix; a breakfast cereal, for example a breakfast cereal with a fruit filling or inclusion; a pet food product for example a dog treat containing berries; or a confectionery product. The confectionery product may be a frozen confectionery product such as an ice-cream or sorbet; a baked confectionery product such as a biscuit, for example a filled biscuit; a chocolate confectionery product such as a filled chocolate sweet; or a sugar-style confectionery product such as a gum, a jelly, a hard-boiled sweet or a chewy sweet. The term sugar-style confectionery product or sugar-style candy refers to confectionery products which would traditionally have been based on sugar, but may be manufactured with alternative sweeteners and/or sugar substitutes. Monosaccharides and disaccharides are commonly present in food materials further processed into confectionery products, for example fructose and glucose in invert sugar or honey, glucose and maltose comprised within hydrolysed corn syrup (known as confectioner's syrup or "glucose syrup") and sucrose added as such. In one embodiment, the food material comprises fruit juice and after the process of the present invention is further processed into a confectionery product. Gums, jellies, hard-boiled sweets and chewy sweets are examples of confectionery products which are often fruit flavoured. Fruit flavoured confectionery products have a greater consumer appeal if they contain real fruit. It is advantageous to be able to provide confectionery products with reduced monosaccharide and/or disaccharide contents, for example confectionery products containing fruit, and so improve their nutritional qualities.

The process of the present invention preferably reduces the monosaccharide and/or disaccharide content in a food material. In one embodiment the total combined monosaccharide and disaccharide content in the food material is reduced by at least 5%, 10%, 20%, 25%, 30%, 35% or 40%.

Where the starting food material comprises sucrose, the process of the present invention preferably reduces the sucrose level in the food material by at least 10%, 20%, 40%, 60%, 80%, 90%, 95%, 96%, 97%, 98% or 99%.

Preferably the process of the invention converts monosaccharides and/or disaccharides in the food material to oligosaccharides and/or polysaccharides.

The oligosaccharides and/or disaccharides may comprise α-1,3 glycosidic bonds and/or α-1,6 and/or α-1,4 glycosidic bonds. Preferably the oligosaccharides and/or disaccharides comprise α-1,3 glycosidic bonds and/or α-1,6 bonds.

The oligosaccharides and/or disaccharides may also comprise α-1,2 glycosidic bonds.

In one embodiment the food material contains at least 5%, 6%, 7%, 8%, 9%, 10%, 15% or 20% oligosaccharides and/or polysaccharides based on the dry weight of the food material, after exposure to the glucosyltransferase.

Sequence Homology/Identity

Homology comparisons can be conducted by eye or, more usually, with the aid of readily available sequence comparison programs. These commercially available computer programs can calculate percentage homology or identity between two or more sequences.

Percentage homology may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion in the nucleotide sequence may cause the following codons to be put out of alignment, thus potentially resulting in a large reduction in percent homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible, reflecting higher relatedness between the two compared sequences, will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example when using the GCG Wisconsin Bestfit package the default gap penalty for amino acid sequences is −12 for a gap and −4 for each extension.

Calculation of maximum percentage homology therefore firstly requires the production of an optimal alignment, taking into consideration gap penalties. A suitable computer program for carrying out such an alignment is the GCG Wisconsin Bestfit package (University of Wisconsin, U.S.A.; Devereux et al. (1984) *Nucleic Acids Res.* 12: 387). Examples of other software that can perform sequence comparisons include, but are not limited to, the BLAST package (see Ausubel et al. (1999) *ibid*-Ch. 18), FASTA (Atschul et al. (1990) *J. Mol. Biol.* 403-410) and the GENE-WORKS suite of comparison tools. Both BLAST and FASTA are available for offline and online searching (see Ausubel et al. (1999) *ibid*, pages 7-58 to 7-60). However, for some applications, it is preferred to use the GCG Bestfit program. Another tool, called BLAST 2 Sequences is also available for comparing protein and nucleotide sequences (see *FEMS Microbiol. Lett.* (1999) 174: 247-50; *FEMS Microbiol. Lett.* (1999) 177: 187-8).

Although the final percentage homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see the user manual for further details). For some applications, it is preferred to use the public default values for the GCG package, or in the case of other software, the default matrix, such as BLOSUM62.

Once the software has produced an optimal alignment, it is possible to calculate percentage homology, preferably percentage sequence identity. The software typically does this as part of the sequence comparison and generates a numerical result.

Those skilled in the art will understand that they can freely combine all features of the present invention described herein, without departing from the scope of the invention as disclosed.

BRIEF DESCRIPTION OF THE FIGURES

Further advantages and features of the present invention are apparent from the following Examples and Figures.

EXAMPLE 1

Methods

Enzymes

Figure 1:
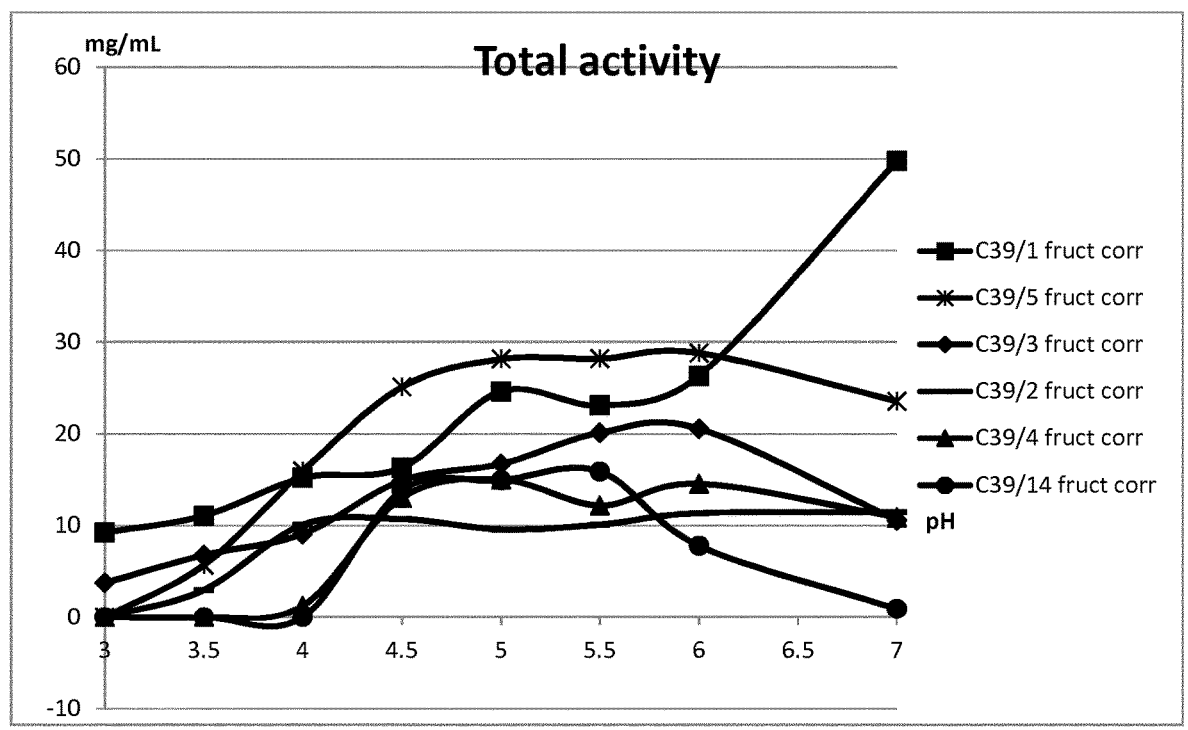
FIG. 1 shows the effect of pH on the total enzyme activity of six different glucosyltransferases. Enzymatic activity was measured by the dextran sucrase activity assay according to Example 1.

The use of different glucosyltransferases (EC 2.4.1.-) was investigated for enzymatic treatments of fruit juice concentrates to reduce the intrinsic sugars by polymerization/transformation into slowly or non-digestible oligosaccharides.

The glucosyltransferases investigated were supplied by Biocatalysts Ltd, UK are shown in Table 1 below:

TABLE 1

| PDN | Accession number | Organism |
| --- | --- | --- |
| C39/1 | Q5SBL9 | *Lactobacillus reuteri* 121 |
| C39/2 | Q5SBN0 | *Lactobacillus reuteri* ML1 |
| C39/3 | Q5SBN3 | *Lactobacillus reuteri* 180 |
| C39/4 | Q5SBM3 | *Lactobacillus sakei* Kg15 |
| C39/5 | Q5SBM8 | *Lactobacillus parabuchneri* |
| C39/14 | Q2I2N5 | *Leuconostoc mesenteroides* |

Chemicals

Glucose, fructose, leucrose, isomaltose, sucrose, isomaltotriose, maltose, panose, maltotriose, maltotetraose and calcium chloride were purchased from Sigma Aldrich USA. Apple juice concentrate and orange juice concentrate were supplied by Austria juice; Ybbstaller fruit Austria and Argoterenas S.A-Industrial citrus, respectively.

Glucosyltransferase Activity

Glucosyltransferase activity ($\mu$ moles of fructose produced per min per 1 g of enzyme powder) was measured according to the dextran sucrase activity assay. Activities were determined by measuring D-glucose and D-fructose release from sucrose at different conditions. The amount of released fructose corresponds to the total activity (total sucrose conversion). The amount of free glucose represents the hydrolytic activity (hydrolysis of sucrose). The transferase activity is represented by the amount of released fructose minus free glucose (sucrose that has been used for transferase reactions). The assay is described below:

Assay

Absorbance: 575 nm; Temperature: 220 C; pH: 4.5; Incubation time: 30 min

Assay Conditions

| pH | 4.5 |
|---|---|
| Temperature | 20° C. |
| Substrate | 6.5% (w/v) sucrose |
| Incubation time | 30 minutes |

Unit Definition

One unit of enzyme activity is defined as that amount of enzyme that causes the release of 1 micromole of glucose equivalents per minute at pH 4.5 and 20° C.

Equipment
Waterbath, set at 20° C.
pH meter
Boiling Bath
Spectrophotometer, set at 540 nm
Timer
P1000 and P5000 pipettes
Glass Test Tubes All equipment is calibrated to the requirements set out in the appropriate EOP, according to the Biocatalysts ISO9001 Manual.

Reagents

Water is RG grade unless otherwise specified.

1. Phosphate/Citrate/$CaCl_2$ Buffer, pH 4.5-stable for 1 month at 15-25° C. 6.6 g di-sodium hydrogen orthophosphate-anhydrous, 5.6 g citric acid.$H_2O$ and 0.055 g $CaCl_2$ is dissolved in approximately 400 ml of RG water. If required, the pH is adjusted to 4.5 with 1M NaOH or 1M citric acid and made up to 500 ml in volumetric flask.

2. Sucrose/$CaCl_2$ Solution 6.5 g of sucrose and 0.011 g $CaCl_2$ is added to a beaker and dissolved in approximately 80 ml of water. 10 ml buffer (1) is added and the solution is made up to a final volume in a volumetric flask.

3. 3-5, Dinitrosalicyclic Acid (DNS)

5 g of DNS is moistened in about 10 ml water. 100 ml 2M sodium hydroxide is added slowly with continuous stirring. 250 ml water is added followed by stirring until completely dissolved. 150 g potassium sodium (+) tartrate is added with stirring until dissolved (slight heating may be required). The solution is made up to a final volume of 500 ml with water in a volumetric flask. Filtration is performed if necessary.

4. 2M Sodium Hydroxide 40 g sodium hydroxide is dissolved in 400 ml water and made up to 500 ml in a volumetric flask.

5. D-Glucose Standard 0.5 g D-glucose is dissolved in approximately 400 ml deionised water and made up to a final volume of 500 ml with RG water in a volumetric flask.

6. Enzyme Samples

Liquid and solid enzymes are first inverted to distribute the sample and weighed in an analytical balance (+/−0.001 g). The enzyme sample is diluted in buffer to a concentration which when assayed gives an absorbance change of between 0.095 and 0.2

Procedure 3 test tubes are labelled for each enzyme sample (2 reactions and a blank). A colour blank and 2 assay standard tubes are also required each time an invertase assay is carried out.

To each of the 3 enzyme analysis tubes 0.5 ml sucrose (2) is added. At this stage the colour blank and standard tubes remain empty. The tubes are placed in a water bath at 20° C. for 5 minutes to equilibrate. For the assay, the following procedure is used:

| | | | Tube | | | |
|---|---|---|---|---|---|---|
| Time/mins | Reagent | Sample 1 | Sample 2 | Enzyme Blank | Glucose Standard 1 | Glucose Standard 2 | Color Blank |
| 0 | Sucrose | 0.5 ml | 0.5 ml | 0.5 ml | — | — | — |
| 5 | Enzyme | 0.5 ml | 0.5 ml | — | — | — | — |
| | | Vortex, and incubate at 20° C. for exactly 30 minutes. | | | | | |
| 35 | DNS | 3 ml | 3 ml | 3 ml | 3 ml | 3 ml | 3 ml |
| | Enzyme | — | — | 0.5 ml | — | — | — |
| | Glucose | — | — | — | 0.5 ml | 0.5 ml | — |
| | Water | — | — | — | 0.5 ml | 0.5 ml | 1 ml |
| | | Vortex, and incubate at 100° C. in boiling bath for 5 minutes. | | | | | |
| 40 | | Remove from boiling bath, and place in 20° C. water bath for 20 mins. | | | | | |
| 60 | | Read absorbance of all tubes at 540 nm, zeroing spectrophotometer with Color Blank. | | | | | |

Calculation

Glucose equivalents ($G$ mg/ml) =

$$\frac{[(\text{Mean } A_{540} \text{ Sample}) - A_{540} \text{ Enzyme blank}] \times 0.5}{(\text{Mean } A_{540} \text{ Glucose Standard})}$$

Where: 0.5 = Amount of glucose present in standard, in mg/ml $$\text{Convert to } \mu\text{mol/min/g} = \frac{G \times 1000 \times 1000 \times DF}{180 \times 30 \times 0.5 \times C}$$

Where:
1000=Conversion of glucose equivalents to μg
1000=Conversion of enzyme concentration to μg
0.5=volume of enzyme (ml)
180=Molecular weight of glucose
30=Reaction time (minutes)
C=Concentration of enzyme (mg/ml)
G =Glucose Equivalents (mg/ml)
DF=Dilution Factor
Therefore:

$$U/g = \frac{G \times 1000 \times 1000 \times DF}{180 \times 30 \times 0.5 \times C}$$
$$= \frac{G \times DF \times 370.37}{C}$$

$$U/ml = \frac{G \times 1000 \times DF}{180 \times 30 \times 0.5}$$
$$= G \times DF \times 0.370$$

Quantification of Free D-glucose and D-fructose Using a Megazyme Kit

To quantify the free D-glucose and D-fructose the K-Frugil kit from Megazyme was used. Samples were first diluted by adding 20 μL sample to 2000 μL mQ water. 60 μL of the diluted sample was transferred to a 96 cell microplate and diluted further with 150 μL mQ water. 60 μL of a reference standard containing 0.2 mg/mL of D-glucose and D-fructose was included in the absorbance measurements and diluted with 150 μL mQ water. The assay was performed according the instructions supplied for the Megazyme kit (K-Frugil., 2012). Absorbance was measured at 340 nm using Varioskan flash multireader 5250510 (Thermo Scientific, USA,) at 25° C.

Qualitative Analysis of Samples Using High-Performance Thin-Layer Chromatography Qualitative analysis of monosaccharides and oligosaccharides in the samples was performed by first diluting the samples 20 times with mQ water and spotting the samples as thin bands with a 1 μL micro syringe (Hamilton) on a HPTLC silica gel 60 plate (20×10 cm, 200 μm) Merck (1.05641.0001) 1 cm above the bottom edge. Standards (1 mg/mL) were also spotted (glucose, fructose, sucrose, isomaltose, panose, isomaltotriose, maltose, maltotriose, maltotetraose, leucrose and hydrolyzed dextran). Two different mobile phases (A and B) were used for different resolutions and contained chloroform, acetic acid and water in different proportions (Vol:Vol:Vol): A (36:42:5, $CHCl_3$: $CH_3COOH$:$H_2O$) B (30:35:11 $CHCl_3$:$CH_3COOH$:$H_2O$).

Quantitative Analysis of oligosaccharides Using HPAEC

Mono and oligosaccharides were analyzed using a Dionex ICS-3000 DC apparatus equipped with an HPLC carbohydrate column.

Screening of glucosyltransferases at Different pHs in Pure sucrose Solutions

Reactions were performed in 1.5 mL Eppendorf tubes by adding 100 μL of citrate-phosphate buffer solution containing 1320 mM sucrose (452 mg/mL) and 100 μL enzyme solution. The final reaction volume was 200 μL containing 660 mM sucrose. Reactions were performed at different pHs (3.0, 3.5, 4.0, 4.5, 5.0, 5.5, 6.0 and 7.0) incubated in a water bath at 30° C. for 30 min. To deactivate the enzyme 10% (v/v) 1M NaOH solution was added (to reach pH 11.0-11.5). To investigate the effect of $Ca^{2+}$ ions on the enzyme, activity reactions were performed in the same way using 100 mM sucrose buffer solutions containing 2 mM $CaCl_2$. The samples were analyzed by the Megazyme kit.

Time Course in Pure sucrose Solution—C39/3

To follow the enzymatic activity over time reactions were performed at an enzyme concentration of 7.23 U/$g_{sucrose}$ at an initial substrate concentration of 660 mM sucrose. The enzyme was first diluted in mQ water containing 0.04% (w/w) NaN3 as preservative. 5 mL citrate-phosphate buffer pH 3.5 (same pH as the juice concentrates) containing 1320 mM sucrose (452 mg/mL) was mixed with 5 mL enzyme solution in a 50 mL Falcon tube and incubated in an oil (Thermal M) bath at 50° C. stirred with a magnetic stirrer. Samples (500 μL) were taken out at the following time points: 0, 30, 60, 120, 180, 240, 300, 1200, 1440 min and deactivated by adding 10% (v/v) 1M NaOH solution. Samples were analyzed by HPLTC and HPAEC.

Optimal Temperature—C39/3

To determine the optimal temperature, for the enzyme C39/3, reactions were performed at an enzyme concentration 7.23 U/$g_{sucrose}$ at an initial substrate concentration of 660 mM sucrose. 200 μL citrate-phosphate buffer containing 1320 mM sucrose (452 mg/mL) pH 4.5 was mixed with 200 μL enzyme solution in 2 mL Eppendorf tubes and incubated in thermo mixers at 45° C., 50° C. and 55° C., 1000 rpm. Samples were taken out of the thermomixers after 60 min and deactivated by adding 10% (v/v) NaOH solution. The samples were analyzed by the Megazyme kit.

Initial Substrate Concentration—C39/3

To evaluate the effect of the initial substrate concentration on the enzyme activity, reactions were performed at an enzyme concentration 7.23 U/$g_{sucrose}$ at initial substrate concentrations of 660 mM, 330 mM and 165 mM sucrose. 200 μL citrate-phosphate buffer 0.1 M containing 1320 mM, 660 mM and 330 mM sucrose pH 3.5 was mixed with 200 μL enzyme solution in 2 mL Eppendorf tubes and incubated in thermomixers at 50° C., 1000 rpm. Samples were taken out of the thermomixers after 300 min and deactivated by adding 10% (v/v) 1M NaOH solution. The samples were analyzed by HPAEC.

Determination of the Optimal Enzyme Concentration for C39/3

To determine the optimal enzyme concentration the following enzyme concentrations were investigated: 1.45, 3.62, 7.23, 14.46, 36.15 and 72.35 U/$g_{sucrose}$ in the presence of 1 mM $CaCl_2$ at an initial substrate concentration of 660 mM sucrose. The enzyme was first diluted in mQ water containing 0.04% (v/v) $NaN_3$. 200 μL citrate-phosphate buffer containing 1320 mM sucrose (452 mg/mL) pH 4.5 was mixed with 200 μL of each enzyme solution and incubated in a thermomixer at 50° C., 1000 rpm. Samples were taken out of the thermomixer at the following time points: 0, 30, 60, 120 and 180 min and deactivated by adding 10% (v/v) 1M NaOH solution. Samples were analyzed for D-glucose and D-fructose content using the Megazyme kit.

Enzymatic Treatment of Fruit Juice Concentrates

Apple and orange juice concentrates were enzymatically treated with the C39/3 enzyme. Reactions were performed at enzyme concentration 14.46 U/$g_{sucrose}$, pH 4.5, 50° C., 1 mM $CaCl_2$, and 0.02% (w/w) $NaN_3$. Samples (~500 μL) were taken at time points t: 0, 30, 60, 90, 120, 150 and 180 min and the enzyme was deactivated by adding 50 μL 10 M NaOH solution. The reactor chambers were 50 mL Schott bottles made of Pyrex glass. Magnetic stirrers were used and the reactor chambers were immersed in temperature controlled oil (Thermal M) baths. The original pH of the juice concentrates was 3.44 for the apple concentrate and 3.55 for the orange concentrate and it was adjusted to 4.5 by adding 2.95% (v/v$_{concentrate}$) of 10M NaOH (for apple concentrate) and 4.55% (v/v$_{concentrate}$) of 10M NaOH (for orange concentrate) to 20 mL juice concentrate. The orange juice concentrate was diluted with 12.5% (v/v$_{concentrate}$) mQ water to enable sufficient stirring. The enzyme concentration (14.46 U/g$_{sucrose}$) was selected based on previous optimization of enzyme sucrose, concentration and the quantity of enzyme added was calculated based on the initial sucrose concentrations: 167.5±16.75 g/L in apple concentrate and 297±29.7 g/L in orange concentrate which was measured by HPAEC. The enzyme was diluted in 250 µL mQ water before added to the concentrates. Samples were analyzed by HPAEC.

To evaluate whether the enzyme C39/3 is deactivated during standard fruit juice pasteurisation conditions 95° C. for 15 sec, the enzyme was incubated in citrate-phosphate buffer (to simulate the juice) at pH 3.0 for 0, 0.25, 0.50, 1, 2, 4, 7 and 10 min. First, 27.19 mg enzyme was dissolved in 200 µL mQ water which corresponds to 116.56 U/mL. 10 µL of the enzyme solution was injected through a septum by a syringe into a glass vial containing 500 µL citrate-phosphate buffer pH 3.0 preheated to 95° C. using a heat block (final enzyme concentration 21.89 U/mL). To measure the residual enzyme activity, 15 µL of the "pasteurized" enzyme solution was mixed with 385 µL citrate-phosphate buffer pH 4.56 solution containing 52.08 mM sucrose, 1.039 mM CaCl$_2$ and 0.02% (w/w) NaN$_3$ as a preservative and incubated in a thermomixer for 30 min at 50° C., 1000 rpm. The final assay conditions were: enzyme concentration 14.46 U/g$_{sucrose}$, sucrose concentration 50 mM and pH 4.5. The samples were deactivated by adding 10% (v/v) 1M NaOH solution and analyzed by Megazyme kit and HPAEC.

Pasteurisation

To simulate a standard fruit juice pasteurisation step which lasts for 15 sec at 95° C. a setup with two oil baths containing two heating coils and one cooling coil were built. First the enzymatically treated orange juice concentrate was diluted with mQ water and the pH was adjusted to 3.0 and 3.5 by addition of 3.2 M citric acid solution, to simulate the pH range of commercial fruit juices. The diluted and pH adjusted juice was pumped at room temperature (23.8° C.) into the system through a silicone tube (4/8 mm internal/outer diameter) by an Ismatec pump (ISM 444) with a flow rate of 96 mL/min (178 rpm). First, the juice passed a preheating coil (volume 68 mL, internal diameter 0.6 cm, length 240 cm) in an thermostat (HAAKE B5/F6) controlled oil bath. The temperature of the oil (Merck S4870800728 1.06900.5000) in the first oil bath were 148° C. The juice entered the second heating coil (volume 24 mL, internal diameter 0.6 cm, Length 85 cm) at 94.6° C. where the actual pasteurisation took place. The temperature of the oil in the second oil bath (Thermo mix BU) was 98.2° C. The juice was cooled in a cooling coil (volume 48 mL, internal diameter 0.45 cm, length 300 cm) directly after the pasteurization to 8.0° C. using an ice bath and tapped on a shott bottle. After the pasteurisation, the juice was reincubated with 50% (w/v) sucrose syrup (filtered 0.2 µm), 31 g/kg$_{final\ juice}$ in a 1 L Das gip fermentor for 6 days at 50° C. The pH was adjusted to 4.5 by adding 10M NaOH solution, to measure residual enzyme activity.

Measurement of Free Calcium Ions

The free Ca$^{2+}$ concentration was determined using a pH/Ion meter device (Metrohm 692) fitted with a perfect ION™ Ca ISE combination calcium electrode (MettlerToledo). Prior to Ca$^{2+}$ measurement, the Ca ISE was calibrated using standard solutions of 1 mmol/L and 10 mmol/L calcium chloride containing 4% (v/v) 2M KCl as ionic strength adjuster.

EXAMPLE 2

Activity at Different pHs

The activity of the enzymes was determined and is shown in Table 2 below.

TABLE 2

| PDN | Accession number | Organism | Activity* (U/g) | Protein*** (mg/g) | Specific activity (U/mg) | Sample size (mg) |
|---|---|---|---|---|---|---|
| C39/1 | Q5SBL9 | Lactobacillus reuteri 121 | 3860 | 598.0 | 6.45 | 700 |
| C39/2 | Q5SBN0 | Lactobacillus reuteri ML1 | 154 | 550.0 | 0.28 | 700 |
| C39/3 | Q5SBN3 | Lactobacillus reuteri 180 | 2475 | 594.0 | 4.17 | 700 |
| C39/4 | Q5SBM3 | Lactobacillus sakei Kg15 | 90 | 572.9 | 0.16 | 700 |
| C39/5 | Q5SBM8 | Lactobacillus parabuchneri | 42 | 534.0 | 0.079 | 700 |
| C39/14 | Q2I2N5 | Leuconostoc mesenteroides | 1589 | 570.8 | 2.78 | 700 |

*Activity measured with dextran sucrase assay
***Protein measured with Bradford assay The six different glucosyltransferases were screened for activity at different pHs in pure sucrose solution. The enzymes concentrations (U/g$_{sucrose}$ and mg/g $_{sucrose}$) are presented in Table 3. The samples were analyzed for D-fructose and D-glucose using the Megazyme kit.

TABLE 3

Equivalence between U/g$_{sucrose}$ and mg$_{protein}$/g$_{sucrose}$ for the six different glucosyltransferases.

| Enzyme | U/g$_{sucrose}$ | mg$_{protein}$/g$_{sucrose}$ |
|---|---|---|
| C39/1 | 0.129 | 0.02 |
| C39/2 | 0.1148 | 0.41 |
| C39/3 | 0.0813 | 0.0195 |
| C39/4 | 0.0528 | 0.33 |
| C39/5 | 0.076 | 0.97 |
| C39/14 | 0.0667 | 0.024 |

Figure 2:
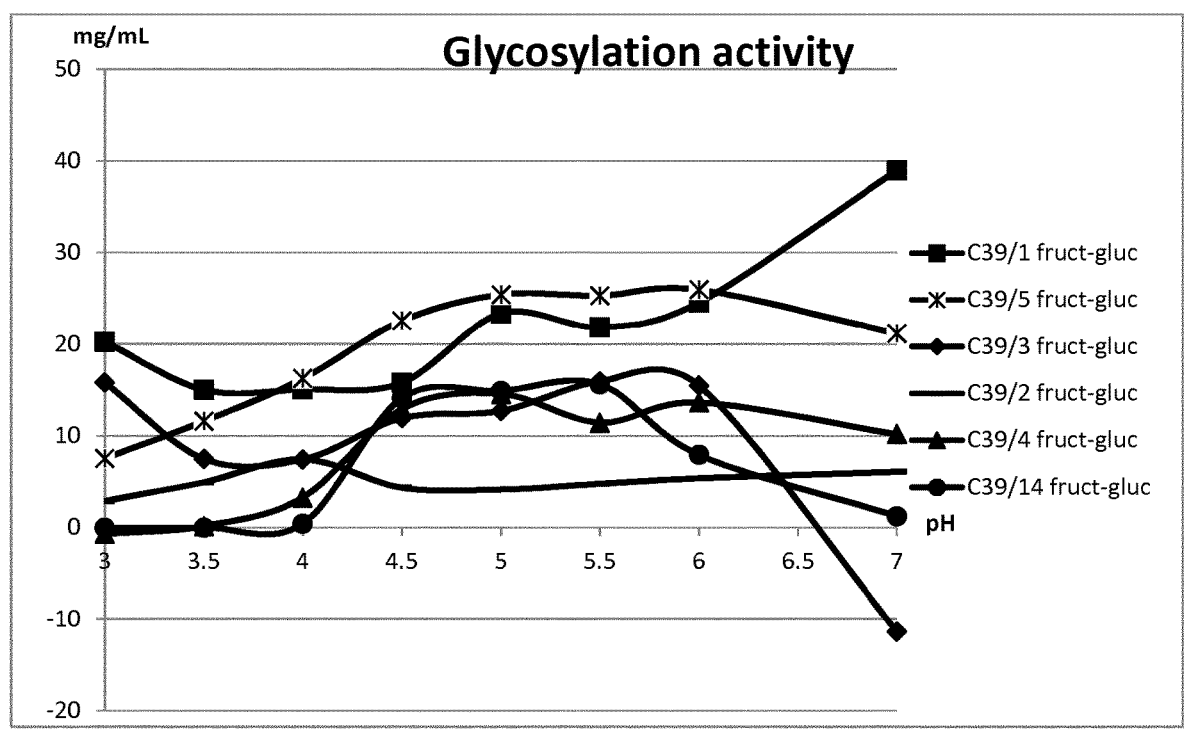
FIG. 2 shows the effect of pH on the glycosylation activity of six different glucosyltransferases.

The results are shown in FIGS. 1 and 2.

The enzyme C39/3 was shown to have very high activity (see Table 2), and it was shown to be active even at low pH (FIGS. 1 and 2).

EXAMPLE 3

Effect of Calcium Ions on the Activity of C39/3

Figure 3:
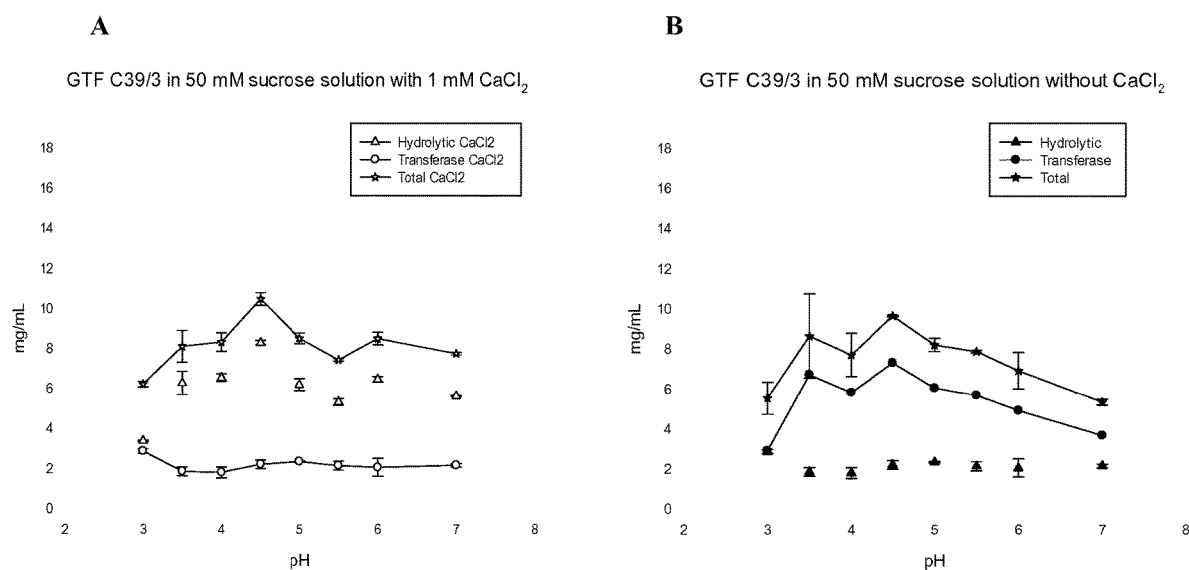
FIG. 3 shows the hydrolytic, transferase and total activities of the enzyme C39/3 in 50 mM sucrose, citrate buffer solution with (panel A) and without (panel B) 1 mM $CaCl_2$.

The hydrolytic, transferase and total activity of the enzyme C39/3 in 50 mM sucrose, citrate-phosphate buffer solution with and without 1 mM CaCl$_2$ is shown in FIG. 3. The average transferase activity, hydrolytic activity, and total activity are 17%, 5% and 13% respectively higher in presence of 1 mM CaCl$_2$ after 30 min.

EXAMPLE 4

Effect of Temperature on the Activity of C39/3

The enzyme was assayed at 45° C., 50° C. and 55° C. The hydrolytic activity at 45° C. and 55° C. is 85% and 90% respectively of the hydrolytic activity at 50° C. The transferase activity at 45° C. and 55° C. is 82% and 76% respectively of the transferase activity at 50° C. in 660 mM sucrose solution. 50° C. is considered as the optimal temperature for the enzyme.

EXAMPLE 5

Effect of Initial Substrate Concentration on the Activity of C39/3

The transferase activity was found to be 68%, 54% and 50% of the total activity in 660 mM, 330 mM and 165 mM sucrose respectively. Thereby the transferase activity is favoured by high substrate concentrations. The % sucrose reduction (approx. 8%) is not affected by the initial sucrose concentration.

EXAMPLE 6

Determination of the Optimal Enzyme Concentration for C39/3

Figure 4:
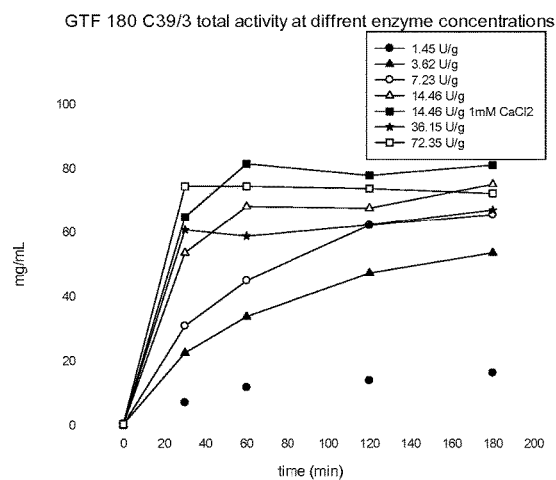
FIG. 4: The determination of optimal enzyme concentration for enzyme C39/3. Panel A shows the total C39/3 activity for different enzyme concentrations. Panel B shows C39/3 transferase activity for different enzyme concentrations. Panel C shows C39/3 hydrolytic activity for different enzyme concentrations. Panel D shows C39/3 activity at an enzyme concentration of 14.46 $U/g_{sucrose}$, with and without 1 mM $CaCl_2$.
Figure 4:
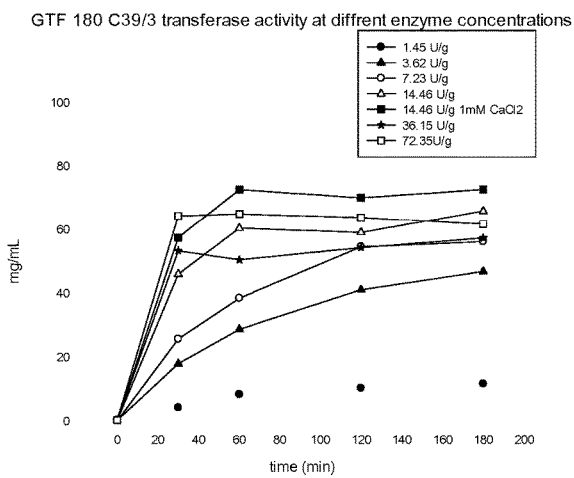
Figure 4:
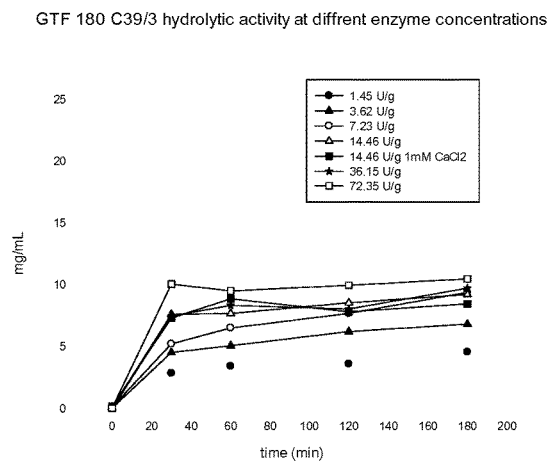
Figure 4:
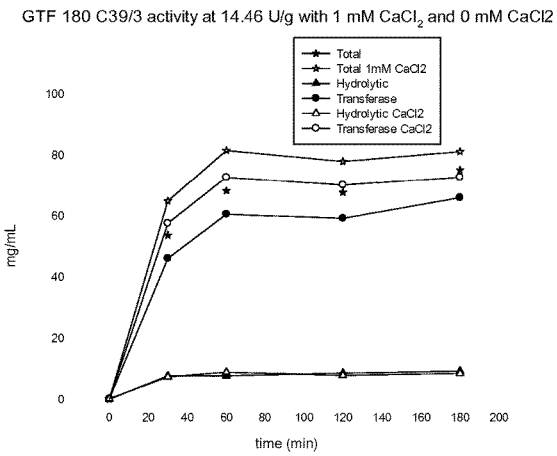

Reactions at different enzyme concentrations were measured. At an enzyme concentration of 72.35 U/g$_{sucrose}$, the total activity reached a maximum of approximately 75 mg$_{fructose}$/mL after 30 min compared to approximately 80 mg/mL after 60 min at an enzyme concentration of 14.46 U/g$_{sucrose}$ with 1 mM CaCl$_2$ (FIG. 4A). The transferase activity was higher at an enzyme concentration of 14.46 U/g$_{sucrose}$ with 1 mM CaCl$_2$ compared to 72.35 U/g$_{sucrose}$ (FIG. 4B). The hydrolytic activity was lower at an enzyme concentration of 14.46 U/g$_{sucrose}$ with 1 mM CaCl$_2$ compared to 72.35 U/g$_{sucrose}$ (FIG. 4C). The average transferase activity, hydrolytic activity, and total activity were 16%, 5% 14% higher, respectively in presence of 1 mM CaCl$_2$ after 30 min (FIG. 4D). The average transferase activity, hydrolytic activity, and total activity are 17%, 15% 17% higher, respectively in presence of 1 mM CaCl$_2$ after 60 min (FIG. 4D). An enzyme concentration of 14.46 U/g$_{sucrose}$ with 1 mM CaCl$_2$ was considered to be optimal.

The equivalence between U/g$_{sucrose}$ and mg$_{protein}$/g$_{sucrose}$ for the enzyme C39/3 (Q5SBN3, from *Lactobacillus reuteri* 180) was determined, see Table 4 below.

TABLE 4

Equivalence between U/g$_{sucrose}$ and mg$_{protein}$/g$_{sucrose}$ for the enzyme C39/3 (Q5SBN3, from *Lactobacillus reuteri* 180).

| U/g$_{sucrose}$ | mg$_{protein}$/g$_{sucrose}$ |
|---|---|
| 72.3 | 29.22 |
| 36.15 | 14.61 |
| 14.46 | 5.844 |
| 7.23 | 2.922 |
| 3.62 | 1.46 |
| 1.45 | 0.584 |

EXAMPLE 7

Figure 5:
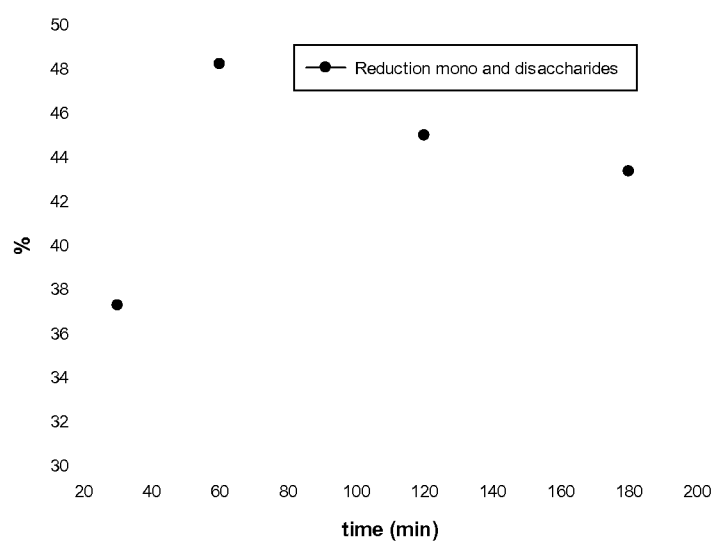
FIG. 5 shows the reduction of mono- and disaccharides catalysed by C39/3 at the optimal enzyme concentration (i.e. 14.46 $U/g_{sucrose}$), in the presence of 1 mM $CaCl_2$.

Quantitative Analysis of Products Created by C39/3 at the Optimal Enzyme Concentration Reaction samples at the optimal enzyme concentration (14.46 U/g$_{sucrose}$ with 1 mM CaCl$_2$) were analyzed by HPAEC. The main products (% mg/mg$_{sucrose}$) are fructose (35.12%) and leucrose (10.45%), followed by glucose (3.85%) and isomaltose (1.41%). The sucrose was reduced to 99.56% and a 48.2% reduction of mono and disaccharides was achieved after 60 min (FIG. 5 and Table 5). The activities by the enzyme are much higher in reality than predicted by the Megazyme kit method because of the formation of leucrose by acceptor reactions which is not detected by the method.

TABLE 5

Concentrations (mg/mL) of mono-, di- and oligosaccharides generated by C39/3 in 660 mM sucrose, citrate-phosphate pH 4.5 buffer solution with 1 mM CaCl$_2$

| time(min) | glucose | fructose | leucrose | isomaltose | sucrose | isomaltotriose | maltose | panose | maltotriose |
|---|---|---|---|---|---|---|---|---|---|
| 0 | 1.38 | 2.15 | 0.00 | 0.00 | 220.72 | 0.15 | 0.00 | 0.00 | 0.00 |
| 30 | 14.70 | 68.21 | 14.84 | 2.06 | 40.91 | 0.39 | 0.00 | 0.00 | 0.00 |
| 60 | 9.85 | 79.33 | 22.95 | 3.11 | 0.96 | 0.56 | 0.00 | 0.23 | 0.00 |
| 120 | 9.41 | 86.52 | 22.78 | 3.46 | 1.29 | 1.06 | 0.00 | 0.26 | 0.00 |
| 180 | 9.82 | 88.56 | 24.27 | 3.83 | 0.63 | 1.27 | 0.00 | 0.26 | 0.00 |

EXAMPLE 8

C39/3 Activity in Apple Juice Concentrate

Figure 6:
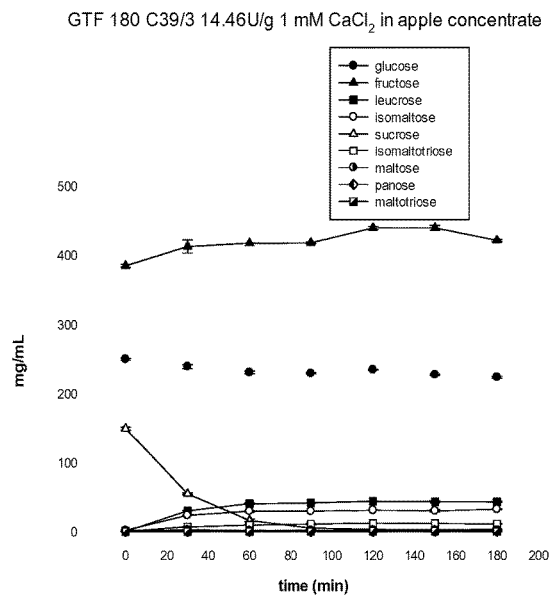
FIG. 6 shows the activity of C39/3 in apple juice concentrate. Panel A shows the change in concentration of mono-, di- and oligosaccharides in apple juice concentrate over time after the addition of enzyme C39/3 (14.46 $U/g_{sucrose}$, in the presence 1 mM $CaCl_2$). The initial sucrose concentration was reduced by 96.75% after 90 min (open triangles). Panel B shows the change in concentration of leucrose, isomaltose, isomaltose triose, maltose, panose and maltotriose. Panel C shows the percentage reduction of mono- and disaccharides in apple juice concentrate catalysed by C39/3; a reduction of 7.9% was achieved after 90 min.
Figure 6:
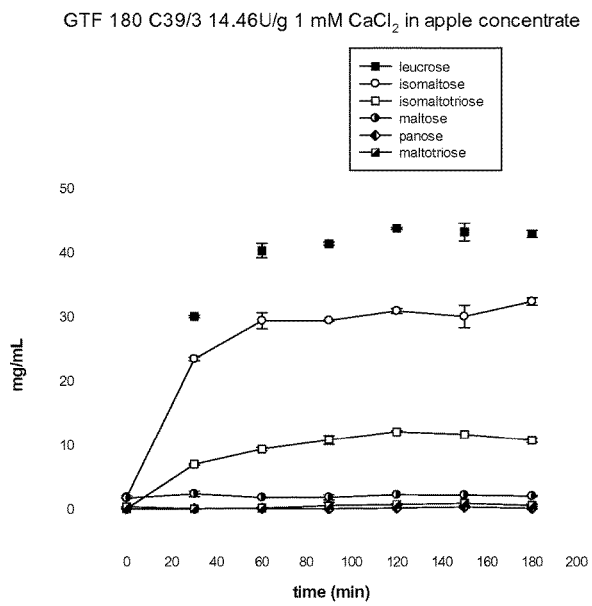
Figure 6:
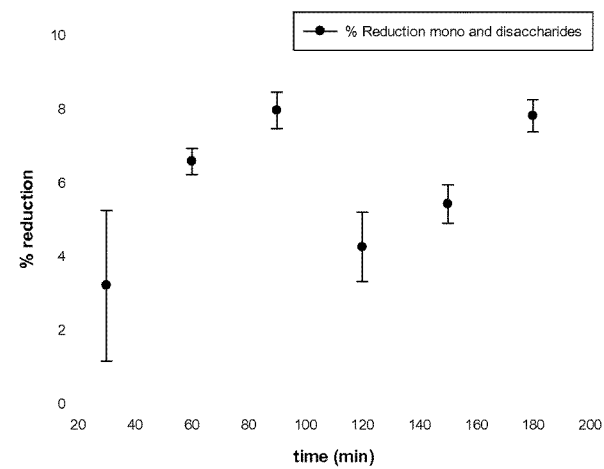

The apple juice concentrate has high initial concentrations of glucose and fructose (249.74±24.97 mg/mL and 384.57±38.46 mg/mL, respectively). The initial sucrose concentration in the apple juice concentrate was measured to be 149.38 mg/mL and was reduced by 96.75% to a concentration of 4.85 mg/mL after 90 minutes. A reduction of mono and disaccharides of 7.9% was achieved after 90 min (FIG. 6A, FIG. 6C and Table 6). The main identified products formed (% mg/mg$_{sucrose}$) were leucrose (28.60%), fructose (23.05%), isomaltose (19.09%) and isomaltotriose (7.45%) (FIG. 6B and Table 6). The high production of leucrose can be explained by the high fructose concentration since fructose act as acceptor molecule in the so called acceptor reaction catalyzed by the enzyme

TABLE 6

Concentrations (mg/mL) of mono-, di- and oligosaccharides generated by C39/3 in apple juice concentrate.

| time(min) | glucose | fructose | leucrose | isomaltose | sucrose | isomaltotriose | maltose | panose | maltotriose |
|---|---|---|---|---|---|---|---|---|---|
| 0 | 249.74 | 384.57 | 0.00 | 1.80 | 149.38 | 0.00 | 1.67 | 0.00 | 0.33 |
| 30 | 239.06 | 412.61 | 30.01 | 23.40 | 54.57 | 6.94 | 2.32 | 0.00 | 0.00 |
| 60 | 230.67 | 417.37 | 40.27 | 29.35 | 16.03 | 9.32 | 1.77 | 0.05 | 0.11 |
| 90 | 229.32 | 417.89 | 41.33 | 29.40 | 4.85 | 10.76 | 1.79 | 0.00 | 0.50 |
| 120 | 234.56 | 439.32 | 43.72 | 30.88 | 3.03 | 12.07 | 2.20 | 0.13 | 0.69 |
| 150 | 227.44 | 439.48 | 43.16 | 30.01 | 2.30 | 11.63 | 2.14 | 0.29 | 0.88 |
| 180 | 223.94 | 421.32 | 42.87 | 32.34 | 3.27 | 10.71 | 1.98 | 0.09 | 0.54 |

EXAMPLE 9

C39/3 Activity in Orange Juice Concentrate

Figure 7:
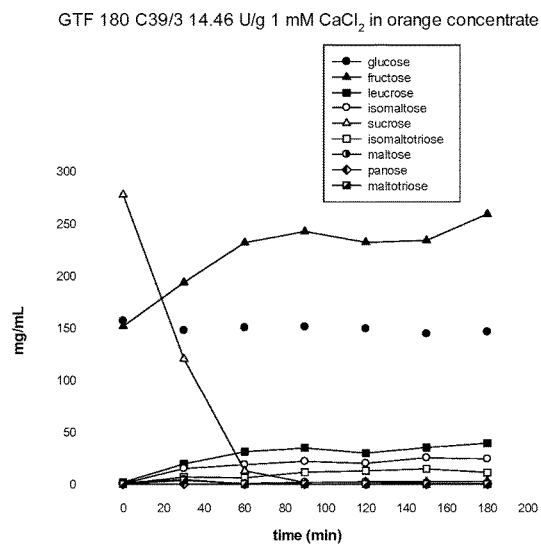
FIG. 7 shows the activity of C39/3 in orange juice concentrate. Panel A shows the change in concentration of mono-, di- and oligosaccharides in orange juice concentrate over time after the addition of enzyme C39/3 (14.46 $U/g_{sucrose}$, in the presence 1 mM $CaCl_2$). The initial sucrose concentration was reduced by 99.46% after 90 min (open triangles). Panel B shows the change in concentration of leucrose, isomaltose, isomaltose triose, maltose, panose and maltotriose. Panel C shows the percentage reduction of mono- and disaccharides in apple juice concentrate catalysed by C39/3; a reduction of 23.2% was achieved after 90 min.
Figure 7:
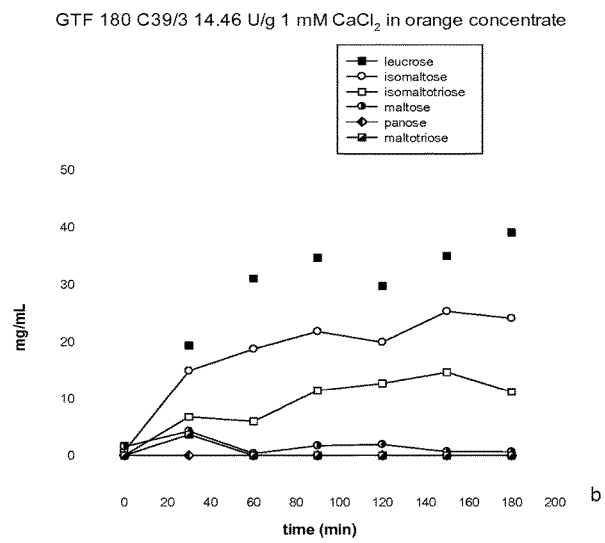
Figure 7:
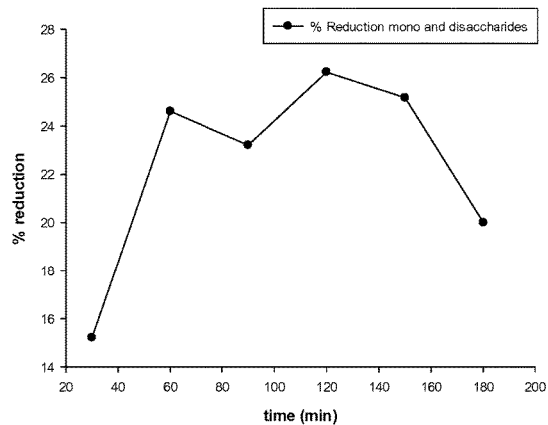

The initial sucrose concentration in the orange juice concentrate was measured to be 277.39 mg/mL and was reduced by 99.46% to a concentration of 1.51 mg/mL after 90 minutes. A reduction of mono and disaccharides of 23.2% was achieved after 90 min (FIG. 7A, FIG. 7C and Table 7). The main products formed (% mg/mg$_{sucrose}$) were fructose (32.90%), leucrose (11.93%) and isomaltose (7.63%) (FIG. 7B and Table 7).

TABLE 7

Concentrations (mg/mL) of mono-, di- and oligosaccharides generated by C39/3 in orange juice concentrate.

| time(min) | glucose | fructose | leucrose | isomaltose | sucrose | isomaltotriose | maltose | panose | maltotriose |
|---|---|---|---|---|---|---|---|---|---|
| 0 | 156.75 | 151.53 | 1.69 | 0.67 | 277.39 | 0.00 | 1.52 | 0.00 | 0.00 |
| 30 | 147.58 | 193.59 | 19.25 | 14.85 | 120.34 | 6.74 | 4.23 | 0.00 | 3.64 |
| 60 | 150.21 | 231.57 | 30.97 | 18.67 | 12.70 | 5.95 | 0.35 | 0.00 | 0.00 |
| 90 | 150.93 | 242.29 | 34.60 | 21.73 | 1.51 | 11.38 | 1.70 | 0.00 | 0.00 |
| 120 | 149.25 | 231.86 | 29.65 | 19.85 | 2.38 | 12.65 | 1.92 | 0.00 | 0.00 |
| 150 | 144.42 | 233.63 | 34.96 | 25.23 | 2.28 | 14.61 | 0.66 | 0.00 | 0.00 |
| 180 | 146.31 | 259.00 | 39.00 | 24.03 | 2.67 | 11.15 | 0.65 | 0.00 | 0.00 |

EXAMPLE 10

C39/1 activity in Orange Juice Concentrate

The enzyme GTF121 C39/1 (referred to herein as C39/1) was also used to treat the orange juice concentrate to compare the sugar reduction and products with products created by the enzyme C39/3.

Figure 8:
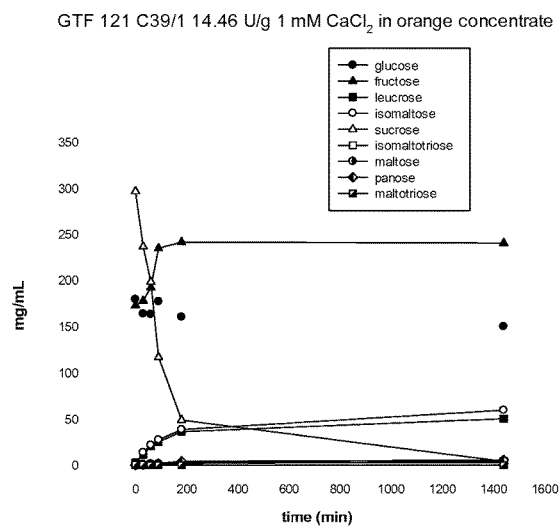
FIG. 8 shows the activity of C39/1 in orange juice concentrate. Panel A shows the change in concentration of mono-, di- and oligosaccharides in orange juice concentrate over time after the addition of C39/1 (14.46 $U/g_{sucrose}$, in the presence 1 mM $CaCl_2$). Panel B shows the change in concentration of leucrose, isomaltose, isomaltose triose, maltose, panose and maltotriose. Panel C shows the percentage reduction of mono- and disaccharides in orange juice concentrate catalsyed by C39/1.
Figure 8:
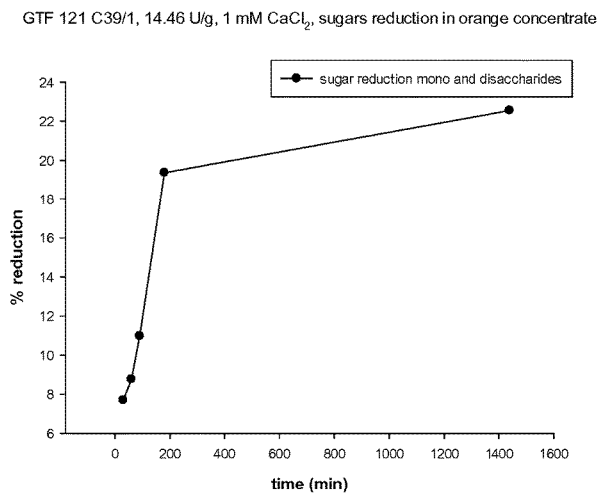
Figure 8:
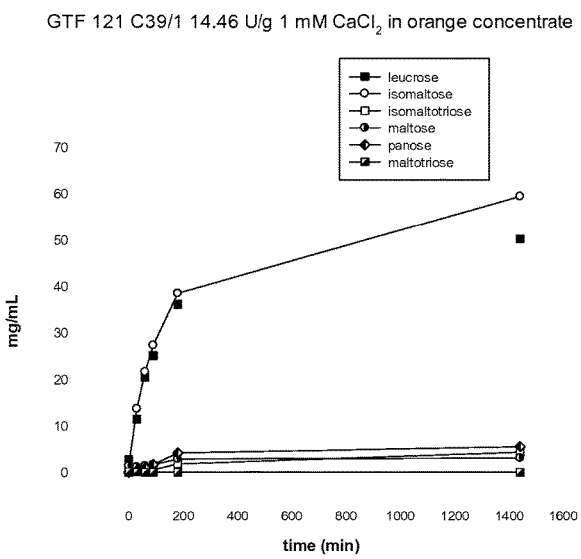

The initial sucrose concentration in the orange juice concentrate was measured to be 296.75 mg/mL and was reduced by 83.60% to a concentration of 48.65 mg/mL after 180 minutes (FIG. 8A and Table 8). A reduction of mono and disaccharides of 19.4% was achieved after 180 min (FIG. 8C). The main products formed (% mg/mg$_{sucrose}$) were fructose (27.64%), isomaltose (14.95%) and leucrose (13.46%) (FIG. 8A, FIG. 8B and Table 8).

TABLE 8

Concentrations (mg/mL) of mono-, di- and oligosaccharides generated by GTF 121 C39/1 in orange juice concentrate.

| time(min) | glucose | fructose | leucrose | isomaltose | sucrose | Isomaltotriose | maltose | panose | maltotriose |
|---|---|---|---|---|---|---|---|---|---|
| 0 | 179.17 | 172.45 | 2.69 | 1.35 | 296.75 | 0.00 | 1.33 | 0.00 | 0.14 |
| 30 | 163.51 | 177.54 | 11.42 | 13.62 | 236.25 | 0.27 | 1.14 | 0.39 | 0.12 |
| 60 | 162.95 | 192.04 | 20.40 | 21.56 | 198.15 | 0.33 | 1.37 | 0.98 | 0.00 |
| 90 | 176.79 | 234.37 | 25.09 | 27.28 | 116.84 | 0.54 | 1.61 | 1.66 | 0.00 |
| 180 | 160.09 | 241.03 | 36.09 | 38.45 | 48.65 | 1.80 | 2.87 | 4.15 | 0.00 |
| 1440 | 149.84 | 239.94 | 50.17 | 59.39 | 3.95 | 4.32 | 3.04 | 5.51 | 0.00 |

The use of C39/3 results in a greater reduction in monosaccharides and disaccharides over the using of C39/1 (compare FIG. 7C and FIG. 8C).

EXAMPLE 11

NMR Analysis of Enzymatic Treated Samples

Samples from determination of optimal enzyme concentration and the enzymatically treated orange and apple juice concentrates were sent for external analysis to Spectral Service AG in Germany. The analysis showed that the linkages in the formed products in apple juice concentrate, orange juice concentrate and sucrose solution are different α-1,6 glycosidic linkages are predominant in apple juice, products in orange juice possesses both α-1,6 and α-1,3 glycosidic linkages. Products with α-1,3 glycosidic linkages are predominant in enzymatically treated 660 mM sucrose citrate-phosphate buffer solution. The presence of α-1,2 glycosidic linkages are present in low amounts in juices and absent in sucrose solution. The analysis also showed that the presence of oligomers was lower in the juice concentrate than in the sucrose citrate-phosphate buffer solution (Table 9).

TABLE 9

Overview of presence of oligomers in samples sent for NMR analysis.

| Sample | Presence of oligomers |
|---|---|
| Orange juice enzymatically treated 60 min C39/3 | Yes low |
| Orange juice control | No |
| Apple juice enzymatically treated 60 min C39/3 | Yes low |
| Apple juice control | No |
| Sucrose 660 mM pH 4.5, 1 mM CaCl$_2$ enzymatically treated 60 min C39/3 | Yes high |

EXAMPLE 12

Free Calcium in Fruit Juice Concentrates

Sucrose reduction by C39/3 was slower in orange juice than in 660 mM sucrose citrate phosphate buffer solution (at pH4.5, 50° C.). One reason for this could be the chelation of $Ca^{2+}$ by different agents present in the fruit juice concentrates (e.g. citrates). Since $Ca^{2+}$ have a stimulating effect on the enzyme activity, the presence of free $Ca^{2+}$ in fruit juice concentrates was investigated.

Measurement in sucrose 660 mM, pH 4.5 citrate-phosphate solution after the addition of 1 mM $Ca^{2+}$ added showed that the free $Ca^{2+}$ concentration was 0.28 mM. The free $Ca^{2+}$ concentration in orange juice concentrate was 0.1 mM after the addition of 1 mM total $Ca^{2+}$ and 0.55 mM after 22.23 mM total $Ca^{2+}$ addition. This can be attributed to the higher concentration of chelating agents (e.g. citric acid) in the fruit concentrate than in the sucrose solution.

The practice of the present invention will employ, unless otherwise indicated, conventional techniques of chemistry, molecular biology, microbiology, recombinant DNA and immunology, which are within the capabilities of a person of ordinary skill in the art. Such techniques are explained in the literature. See, for example, J. Sambrook, E. F. Fritsch, and T. Maniatis, 1989, *Molecular Cloning: A Laboratory Manual*, Second Edition, Books 1-3, Cold Spring Harbor Laboratory Press; Ausubel, F. M. et al. (1995 and periodic supplements; *Current Protocols in Molecular Biology*, ch. 9, 13, and 16, John Wiley & Sons, New York, N.Y.); B. Roe, J. Crabtree, and A. Kahn, 1996, *DNA Isolation and Sequencing: Essential Techniques*, John Wiley & Sons; J. M. Polak and James O'D. McGee, 1990, *In Situ Hybridization: Principles and Practice;* Oxford University Press; M. J. Gait (Editor), 1984, *Oligonucleotide Synthesis: A Practical Approach*, Irl Press; D. M. J. Lilley and J. E. Dahlberg, 1992, *Methods of Enzymology: DNA Structure Part A: Synthesis and Physical Analysis of DNA* Methods in Enzymology, Academic Press; and E. M. Shevach and W. Strober, 1992 and periodic supplements, *Current Protocols in Immunology*, John Wiley & Sons, New York, N.Y. Each of these general texts is herein incorporated by reference.

The invention claimed is:

1. A process for reducing the monosaccharide and/or disaccharide content in a food material, the process comprising reducing the sucrose level in the food material by at least 95% by contacting the food material with calcium chloride having a concentration of 0.8-1.2 mM and a glucosyltransferase having a concentration of 12 to 18 U/g sucrose, at a pH between 3 and 3.5, the glucosyltransferase comprising an amino acid sequence having 100% identity to SEQ ID NO:1,
the food material comprises orange juice, and
the glucosyltransferase is the only enzyme that caused the reducing of the sucrose level in the food material by at least 95%.

2. The process according to claim 1 comprising the glucosyltransferase converting monosaccharides and/or disaccharides in the food material to oligosaccharides and/or polysaccharides.

3. The process according to claim 2, wherein the oligosaccharides comprise α-1,3 glycosidic bonds and/or α-1,6 glycosidic bonds.

4. The process according to claim 2, wherein the oligosaccharides comprise α-1,2 glycosidic bonds.

5. The process according to claim 1 comprising immobilizing the glucosyltransferase on a support.

6. The process according to claim 1 comprising reducing the total combined monosaccharide and disaccharide content in the food material by at least 5%.

7. The process according to claim 1 comprising reducing the total combined monosaccharide and disaccharide content in the food material by at least 10%.

8. The process according to claim 1, wherein the food material contains at least 5% oligosaccharides based on the dry weight of the food material, after exposure to the glucosyltransferase.

9. A method for reducing the monosaccharide and/or disaccharide content and/or increasing the oligosaccharide content of a food material, the method comprising reducing the sucrose level in the food material by at least 95% by contacting the food material with calcium chloride having a concentration of 0.8-1.2 mM and a glucosyltransferase having a concentration of 12 to 18 U/g sucrose, at a pH between 3 and 3.5, the glucosyltransferase comprising an amino acid sequence having 100% identity to SEQ ID NO:1,
the food material comprises orange juice, and
the glucosyltransferase is the only enzyme that caused the reducing of the sucrose level in the food material by at least 95%.

10. The process according to claim 1, wherein the process is carried out at a temperature from about 45° C. to about 60° C.

11. The process according to claim 5 further comprising terminating the reduction by removing the immobilized glucosyltransferase from contact with the food material.

12. The process according to claim 1 comprising processing the food material into a food product after the contacting the food material with the calcium chloride and the glucosyltransferase, wherein the food product is selected from the group consisting of a fruit yoghurt, a powdered fruit beverage mix, a breakfast cereal with a fruit filling or inclusion, a dog treat containing berries, a frozen confectionery product, a baked confectionery product, a chocolate confectionery product, a sugar-style confectionery product, and combinations thereof.

13. The method according to claim 9 comprising processing the food material into a food product after the contacting the food material with the calcium chloride and the glucosyltransferase, wherein the food product is selected from the group consisting of a fruit yoghurt, a powdered fruit beverage mix, a breakfast cereal with a fruit filling or inclusion, a dog treat containing berries, a frozen confectionery product, a baked confectionery product, a chocolate confectionery product, a sugar-style confectionery product, and combinations thereof.

14. The process according to claim 1, wherein the calcium chloride is present at a concentration of about 1 mM.

15. The process according to claim 1, wherein the glucosyltransferase is present at a concentration of about 5.8 mg glucosyltransferase/g sucrose.

* * * * *